United States Patent
Dunning et al.

(10) Patent No.: US 8,845,704 B2
(45) Date of Patent: Sep. 30, 2014

(54) VISIBLE LIGHT MODULATION OF MITOCHONDRIAL FUNCTION IN HYPOXIA AND DISEASE

(71) Applicant: Clarimedix Inc., Boulder, CO (US)

(72) Inventors: John Dunning, Boulder, CO (US); Vivian Dullien, Boulder, CO (US); Robert O. Poyton, Lafayette, CO (US); Richard Samuel Murdoch, Albuquerque, NM (US)

(73) Assignee: Clarimedix Inc., Boulder, CO (US)

( * ) Notice: Subject to any disclaimer, the term of this patent is extended or adjusted under 35 U.S.C. 154(b) by 0 days.

(21) Appl. No.: 13/846,632

(22) Filed: Mar. 18, 2013

(65) Prior Publication Data
US 2013/0288328 A1 Oct. 31, 2013

Related U.S. Application Data

(63) Continuation of application No. 12/599,797, filed as application No. PCT/US2008/063454 on May 12, 2008, now abandoned.

(60) Provisional application No. 61/012,300, filed on Dec. 7, 2007, provisional application No. 60/917,385, filed on May 11, 2007.

(51) Int. Cl.
*A61N 5/06* (2006.01)

(52) U.S. Cl.
USPC .................................. 607/88; 607/89; 607/90

(58) Field of Classification Search
USPC ...................................... 128/898; 607/88–94
See application file for complete search history.

(56) References Cited

U.S. PATENT DOCUMENTS

| | | | |
|---|---|---|---|
| 5,400,425 A | 3/1995 | Nicholas et al. | |
| 6,218,366 B1 | 4/2001 | St. Cyr et al. | |
| 6,803,233 B2 | 10/2004 | Lynch et al. | |
| 7,107,997 B1 | 9/2006 | Moses et al. | |
| 7,150,710 B2 | 12/2006 | Haber et al. | |
| 7,303,578 B2 | 12/2007 | De Taboada et al. | |
| 7,309,348 B2 | 12/2007 | Streeter et al. | |
| 7,316,922 B2 | 1/2008 | Streeter | |
| 7,344,555 B2 | 3/2008 | Anders et al. | |
| 7,374,569 B2 | 5/2008 | Whatcott et al. | |
| 7,526,344 B2* | 4/2009 | Kim ............................. | 607/138 |

(Continued)

FOREIGN PATENT DOCUMENTS

| | | |
|---|---|---|
| CN | 1658804 A | 8/2005 |
| WO | 03/086215 A1 | 10/2003 |

(Continued)

OTHER PUBLICATIONS

Baynes, "Role of Oxidative Stress in Development of Complications in Diabetes," *Diabetes* 40:405-412, Apr. 1991.

(Continued)

*Primary Examiner* — Bill Thomson
*Assistant Examiner* — Jeffrey Lipitz
(74) *Attorney, Agent, or Firm* — Seed IP Law Group PLLC

(57) ABSTRACT

The present invention provides methods of using electromagnetic radiation in the visible portion of the spectrum to modulate mitochondrial function in the treatment of various conditions, including Alzheimer's disease, other dementias, hypoxia and diabetic peripheral neuropathy, and sensory disorders of the extremities.

19 Claims, 8 Drawing Sheets

(56) References Cited

U.S. PATENT DOCUMENTS

| | | | |
|---|---|---|---|
| 7,534,255 B1 | 5/2009 | Streeter et al. | |
| 7,540,869 B2 | 6/2009 | Altshuler et al. | |
| 7,559,945 B2 | 7/2009 | Breden et al. | |
| 7,575,589 B2 | 8/2009 | De Taboada et al. | |
| 2004/0044384 A1 | 3/2004 | Leber et al. | |
| 2004/0230252 A1 | 11/2004 | Kullok et al. | |
| 2004/0260367 A1 | 12/2004 | De Taboada et al. | |
| 2005/0054908 A1* | 3/2005 | Blank et al. | 600/316 |
| 2005/0267090 A1 | 12/2005 | Mascharak | |
| 2006/0074282 A1 | 4/2006 | Ward et al. | |
| 2006/0161226 A1* | 7/2006 | McMickle | 607/88 |
| 2006/0184214 A1 | 8/2006 | McDaniel | |
| 2006/0253177 A1 | 11/2006 | Taboada et al. | |
| 2006/0293719 A1 | 12/2006 | Naghavi | |
| 2007/0096352 A1 | 5/2007 | Cochran et al. | |
| 2007/0123844 A1* | 5/2007 | Henry | 606/4 |
| 2007/0179570 A1 | 8/2007 | De Taboada et al. | |
| 2007/0179571 A1 | 8/2007 | De Taboada et al. | |
| 2007/0213792 A1 | 9/2007 | Yaroslavsky et al. | |
| 2007/0233208 A1 | 10/2007 | Kurtz et al. | |
| 2008/0107603 A1 | 5/2008 | Aruoma | |
| 2009/0216301 A1 | 8/2009 | Streeter et al. | |
| 2009/0254154 A1 | 10/2009 | De Taboada et al. | |

FOREIGN PATENT DOCUMENTS

| | | |
|---|---|---|
| WO | 2005/011606 A2 | 2/2005 |
| WO | 2007/047892 A1 | 4/2007 |
| WO | 2008/017975 A1 | 2/2008 |
| WO | 2008/044060 A1 | 4/2008 |
| WO | 2008/141296 A1 | 11/2008 |

OTHER PUBLICATIONS

Baynes et al., "Role of Oxidative Stress in Diabetic Complications: A New Perspective on an Old Paradigm," *Diabetes* 48:1-9, Jan. 1999.
Beal, "Oxidative metabolism," *Ann. NY Acad. Sci.* 924:164-169, 2000, 7 pages.
Beauvoit et al., "Contribution of the Mitochondrial Compartment to the Optical Properties of the Rat Liver: A Theoretical and Practical Approach," *Biophysical Journal* 67:2501-2510, Dec. 1994.
Brown et al., "Nitric oxide and mitochondrial respiration in the heart," *Cardiovascular Research* 75:283-290, 2007.
Capla et al., "Diabetes Impairs Endothelial Progenitor Cell-Mediated Blood Vessel Formation in Response to Hypoxia," *Plastic and Reconstructive Surgery* 119(1):59-70, Jan. 2007.
Castello et al., "Mitochondrial cytochrome oxidase produces nitric oxide under hypoxic conditions: Implications for oxygen sensing and hypoxic signaling in eukaryotes," *Cell Metab.* 3:277-287, Apr. 2006.
Castello et al., "Oxygen-regulated isoforms of cytochrome $c$ oxidase have differential effects on its nitric oxide production and on hypoxic signaling," *PNAS* 105(24):8203-8208, Jun. 17, 2008.
Chandel et al., "Reactive Oxygen Species Generated at Mitochondrial Complex III Stabilize Hypoxia-inducible Factor-1α during Hypoxia: A Mechanism of $O_2$ Sensing," *J. Biol. Chem.* 275(33):25130-25138, Aug. 18, 2000.
Colton et al., "NO synthase 2 (*NOS2*) deletion promotes multiple pathologies in a mouse model of Alzheimer's disease," *PNAS* 103(34):12867-12872, Aug. 22, 2006, 8 pages.
Communication pursuant to Article 94(3) EPC, for corresponding European Patent Application No. 08 769 457.6-2305, dated Jun. 29, 2011, 5 pages.
Communication pursuant to Article 94(3) EPC, for corresponding European Patent Application No. 09 793 208.1-2305, dated Dec. 13, 2012, 4 pages.
Conlan et al., "Biostimulation of wound healing by low-energy laser irradiation: A review," *J. Clin. Periodontol.* 23:492-496, 1996.
Corker et al., "Nitric Oxide Formation by *Escherichia coli*," *The Journal of Biological Chemistry* 278(34):31584-31592, Aug. 22, 2003.
DeLellis et al., 2004.

DeLellis et al., "Improved Sensitivity in Patients with Peripheral Neuropathy: Effects of Monochromatic Infrared Photo Energy," *J. Am. Podiatr. Med. Assoc.* 95(2):143-147, Mar./Apr. 2005.
Diabetes Control and Complications Trial Research Group, "The Effect of Intensive Treatment of Diabetes on the Development and Progression of Long-Term Complications in Insulin-Dependent Diabetes Mellitus," *New Eng. J. Med.* 329(14):977-986, Sep. 30, 1993.
Diabetes Control and Complications Trial Research Group, "Effect of Intensive Diabetes Treatment on Nerve Conduction in the Diabetes Control and Complications Trial," *Ann. Neurol.* 38(6):869-880, Dec. 1995.
Diabetes Control and Complications Trial/Epidemiology of Diabetes Interventions and Complications Research Group, "Effect of Intensive Therapy on the Microvascular Complications of Type 1 Diabetes Mellitus," *JAMA* 287(19):2563-2569, May 15, 2002.
Dirmeier et al., "Exposure of Yeast Cells to Anoxia Induces Transient Oxidative Stress: Implications for the Induction of Hypoxic Genes," *J. Biol. Chem.* 277(38):34773-34784, Sep. 20, 2002.
Eells et al., "Therapeutic photobiomodulation for methanol-induced retinal toxicity," *PNAS* 100(6):3439-3444, Mar. 18, 2003.
Eells et al., "Mitochondrial signal transduction in accelerated wound and retinal healing by near-infrared light therapy," *Mitochondrion* 4:559-567, 2004.
Fukuyama et al., "beta-Amyloid polypeptide increases calcium-uptake in PC12 cells: a possible mechanism for its cellular toxicity in Alzheimer's disease," *Brain Res.* 667(2):269-272, Dec. 26, 1994. Abstract provided, 1 pages.
Giulivi et al., "Production of Nitric Oxide by Mitochondria," *The Journal of Biological Chemistry* 273(18):11038-11043, May 1, 1998.
Grishko et al., "Hypoxia promotes oxidative base modifications in the pulmonary artery endothelial cell VEGF gene," *The FASEB Journal*, published online Mar. 20, 2001, 21 Pages.
Harkless et al., "Improved foot sensitivity and pain reduction in patients with peripheral neuropathy after treatment with monochromatic infrared photo energy—MIRE," *Journal of Diabetes and Its Complications* 20:81-87, 2006.
International Preliminary Report on Patentability, issued Nov. 17, 2009, for PCT/US2008/063454, 6 pages.
International Preliminary Report on Patentability, issued Apr. 5, 2011, for PCT/US2009/059104, 7 pages.
International Search Report, mailed Oct. 7, 2008, for PCT/US2008/063454, 2 pages.
International Search Report and Written Opinion, mailed Dec. 28, 2009, for PCT/US2009/059104, 14 pages.
Itoh et al., "Dynorphin A-(1-13) markedly improves scopolamine-induced impairment of spontaneous alternation performance in mice," *Eur. J. Pharmacol.* 236(3):341-345, Jun. 4, 1993. Abstract provided, 1 page.
Karu, "Primary and secondary mechanisms of action of visible to near-IR radiation on cells," *J. Photochem. Photobiol. B: Biol* 49:1-17, 1999.
Karu et al., "Photobiological modulation of cell attachment via cytochrome c oxidase," *Photochem. Photobiol. Sci.* 3:211-216, 2004.
Karu et al., "Absorption measurements of a cell monolayer relevant to phototherapy: Reduction of cytochrome $c$ oxidase under near IR radiation," *J. Photochem. Photobiol. B: Biology* 81:98-106, 2005.
Lee et al., "cAMP-dependent Tyrosine Phosphorylation of Subunit I Inhibits Cytochrome $c$ Oxidase Activity," *J. Biol. Chem.* 280(7):6094-6100, 2005.
Lowell et al., "Mitochondrial Dysfunction and Type 2 Diabetes," *Science* 307:384-387, Jan. 21, 2005.
Mattson et al., *Alzheimer's Dis. Rev.* 12:1-14, 1997.
Oakley et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation," *J. Neurosci.* 26(40):10129-10140, Oct. 4, 2006.
Palm, "Intrarenal Oxygen in Diabetes and a Possible Link to Diabetic Nephropathy," *Clinical and Experimental Pharmacology and Physiology* 33:997-1001, 2006.
Perry et al., "Alzheimer Disease and Oxidative Stress," *J. Biomed. Biotechnol.* 2(3):120-123, 2002.

(56) References Cited

OTHER PUBLICATIONS

Polidori et al., "Hallmarks of protein oxidative damage in neurodegenerative diseases: focus on Alzheimer's disease," *Amino Acids* 32:553-559, Feb. 2, 2007.
Pop-Busui et al., "Diabetic neuropathy and oxidative stress," *Diabetes/Metabolism Research and Reviews* 22:257-273, 2006.
Powell et al., "Reversal of Diabetic Peripheral Neuropathy and New Wound Incidence: The Role of MIRE," *Adv. Skin Wound Care* 17(6):295-300, Jul./Aug. 2004.
Powell et al., "Reversal of diabetic peripheral neuropathy with phototherapy (MIRE™) decreases falls and the fear of falling and improves activities of daily living in seniors," *Age and Ageing* 35:11-16 and 454, Jan. 2006, 7 Pages.
Poyton et al., "Expression and Function of Cytochrome *c* Oxidase Subunit Isologues: Modulators of Cellular Energy Production?" *Ann. NY Acad. Sci.* 550:289-307, 1988, 20 pages.
Poyton et al., "Crosstalk Between Nuclear and Mitochondrial Genomes," *Annu. Rev. Biochem.* 65:563-607, 1996.
Poyton, "Assembling a time bomb—cytochrome *c* oxidase and disease," *Nature Genetics* 20:316-317, Dec. 20, 1998.
Poyton, "Models for oxygen sensing in yeast: implications for oxygen-regulated gene expression in higher eucaryotes," *Respir. Physiol.* 115(2):119-133, 1999.
Prabu et al., "Protein Kinase A-mediated Phosphorylation Modulates Cytochrome *c* Oxidase Function and Augments Hypoxia and Myocardial Ischemia-Related Injury," *J. Biol. Chem.* 281(4):2061-2070, Jan. 27, 2006.
Pschenitzka et al., "Excitation mechanisms in dye-doped organic light-emitting devices," *Applied Physics Letters* 79(26):4354-4356, Dec. 24, 2001.
Quinn et al., "Beta-amyloid plaques induce neuritic dystrophy of nitric oxide-producing neurons in a transgenic mouse model of Alzheimer's disease," *Exp. Neurol.* 168(2):20312, Apr. 2001. Abstract provided, 1 page.
Rolo et al., "Diabetes and mitochondrial function: Role of hyperglycemia and oxidative stress," *Toxicol and Applied Pharmacol.* 212:167-178, 2006.
Ryan et al., "Mitochondrial-Nuclear Communications," *Annu. Rev. Biochem.* 76:701-722, 2007.
Schon et al., *J. Clin. Invest.* 111(3):303-312, 2003.
Selkoe, "Amyloid β-Protein and the Genetics of Alzheimer's Disease," *J. Biol. Chem.* 271(31):18295-18298, Aug. 2, 1996.
Selkoe, "Alzheimer's Disease: Genes, Proteins, and Therapy," *Physiol. Rev.* 81(2):741-766, Apr. 2001.
Sherrington et al., "Alzheimer's disease associated with mutations in presenilin 2 is rare and variably penetrant," *Hum. Mol. Genet.* 5(7):985-988, 1996.
Sommer et al., "Biostimulatory Windows in Low-Intensity Laser Activation: Lasers, Scanners, and NASA's Light-Emitting Diode Array System," *J. Clin. Laser Med. Surg.* 19(1):29-33, 2001.
Tachtsidis et al., "Investigation of in vivo measurement of cerebral cytochrome-*c*-oxidase redox changes using near-infrared spectroscopy in patients with orthostatic hypotension," *Physiol. Meas.* 28:199-211, 2007.
Takahashi et al., "Hypoxia Enhances S-Nitrosylation-Mediated NMDA Receptor Inhibition via a Thiol Oxygen Sensor Motif," *Neuron* 53:53-64, Jan. 4, 2007.
Whelan et al., "Effect of NASA Light-Emitting Diode Irradiation on Wound Healing," *J. Clin. Laser Med. Surg.* 19(6):305-314, 2001.
Whelan et al., "NASA Light-Emitting Diodes for the Prevention of Oral Mucositis in Pediatric Bone Marrow Transplant Patients," *J. Clin. Laser Med. Surg.* 20(6):319-324, 2002.
Winterle et al., "Photoreactions of Cytochrome *c* Oxidase," *Photochem. Photobiol.* 82:711-719, 2006.
Wong-Riley et al., "Light-emitting diode treatment reverses the effect of TTX on cytochrome oxidase in neurons," *Neurochemistry NeuroReport* 12(14):3033-3037, Oct. 8, 2001.
Wong-Riley et al., "Photobiomodulation Directly Benefits Primary Neurons Functionally Inactivated by Toxins: Role of Cytochrome *c* Oxidase," *J. Biol. Chem.* 280(6):4761-4771, Feb. 11, 2005.
Written Opinion, mailed Oct. 7, 2008, for PCT/US2008/063454, 5 pages.
Wu et al., "Efficient organic electroluminescent devices using single-layer doped polymer thin films with bipolar carrier transport abilities," *IEEE Transactions on Electron Devices* 44:1269-1281, 1997.
Yu et al., "Effects of Photostimulation on Wound Healing in Diabetic Mice," *Lasers Surg. Med.* 20:56-63, 1997.
Zhang et al., "Study of near infrared technology for intracranial hemotoma detection," *Journal of Biomedical Optics* 5(2):206-213, Apr. 2000.
Zhu et al., "Nicotine Modulates Evoked GABAergic Transmission in the Brain," *J. Neurophysiol.* 82:3041-3045, 1999.

\* cited by examiner

VISIBLE LIGHT MODULATION OF MITOCHONDRIAL FUNCTION IN HYPOXIA AND DISEASE

CROSS REFERENCE TO RELATED APPLICATIONS

This application is a continuation of U.S. patent application Ser. No. 12/599,797 filed Sep. 1, 2010, now pending; which is a U.S. national stage application filed under 35 U.S.C. §371 of International Patent Application No. PCT/US2008/063454 accorded, an international filing date of May 12, 2008; which claims the benefit of U.S. Provisional Application No. 61/012,300, filed Dec. 7, 2007, and U.S. Provisional Application No. 60/917,385, filed May 11, 2007; all of which applications are incorporated herein by reference in their entirety.

BACKGROUND

Photobiomodulation, using light emitting diode (LEDs) arrays or low energy lasers, has been reported to have a variety of therapeutic benefits (Conlan et al. 1996; Sommer et al. 2001; Whelan et al. 2001; Yu et al. 1997; Delellis et al. 2005; Powell et al. 2004; Harkless et al. 2006; Powell et al. 2006). This non-invasive therapy has been used to accelerate wound healing, improve recovery rates from ischemia, slow degeneration of injured optic nerves, and improve sensitivity and reduce pain in various types of peripheral neuropathies including those associated with diabetes.

Diabetes is a common metabolic disorder that is rapidly becoming an epidemic worldwide (Lowell and Schulman, 2005). In the United States, Type II diabetes is the leading cause of blindness. Diabetic peripheral neuropathies are some of the most common long-term complications of diabetes (Pop-Busui et al. 2006). They are a major cause of pain associated with diabetes and often result in lower extremity amputations. Although studies have reported that many patients with diabetic peripheral neuropathies are responsive to near infrared radiation (NIR) therapy (Delellis et al. 2004; Powell et al. 2004; Harkless et al. 2006; Powell et al. 2006) the therapeutic mode of action of photobiomodulation in treating these neuropathies is not yet clear.

NIR is effective in these therapies. Light in the NIR has significant advantages over visible or ultraviolet light because it penetrates tissues more deeply than visible light and at the same time lacks the carcinogenic and mutagenic properties of ultraviolet light (Whelan et al., 2001, 2002). The cellular and molecular mechanisms that underlie the therapeutic benefits of NIR are still poorly understood. However, several studies have revealed that the most effective wavelengths for therapeutic photobiomodulation are between 600 and 830 nm (Karu, 1999; Karu, 2005).

Until recently, mitochondrial cytochrome c oxidase was thought to have only one enzymatic activity; the reduction of oxygen to water. This reaction occurs under normoxic conditions and involves the addition of 4 electrons and 4 protons to diatomic oxygen. During this process oxygen is reduced by a series of one electron transfers. The first electron added to oxygen produces superoxide ($O_2^-$), the second electron produces peroxide ($H_2O_2$), the third electron added produces the hydroxyl ion ($OH^-$), and the fourth electron produces water. Superoxide, hydrogen peroxide, and the hydroxyl ion are incompletely reduced forms of oxygen and are referred to collectively as reactive oxygen species (ROS). ROS are normally sequestered at the binuclear reaction center within the holocytochrome c oxidase molecule and are not released. However, under some pathological conditions (Poyton, 1999) they are released and can either act destructively (to induce oxidative stress, a condition that lies at the heart of many diseases as well as aging), or constructively (in intracellular signaling pathways (Poyton and McEwen, 1996)). Because light can affect the oxidation state of cytochrome c oxidase (Winterrle and Einarsdottir, 2006, Tachtsidis et al. 2007) it can also alter the conformation of the binuclear reaction center and cause the release of reactive oxygen species.

It is now clear that the mitochondrial respiratory chain and mitochondrial cytochrome c oxidase can have profound effects on cell growth, aging, and the induction of a large number of nuclear genes when cells experience low oxygen levels (Poyton and McEwen, 1996; Castello et al. 2006; Ryan and Hoogenraad, 2007). These effects are brought about by signaling pathways between the mitochondrion and nucleus. Although these pathways are still incompletely understood there is now compelling evidence that superoxide ($O_2^-$) nitric oxide (NO), and peroxynitrite ($ONOO^-$) (formed by the reaction of NO with $O_2^-$) are involved. The peroxynitrite generated from NO and superoxide is capable of affecting protein tyrosine nitration, which, in turn, may alter specific proteins involved in mitochondrial-nuclear signaling pathways.

In order to better understand and treat disease by photobiomodulation it is important to identify important quantifiable biomarkers that are affected by the disease and subsequently altered by light therapy. This invention provides for these and other needs by disclosing such predictive biomarkers but also in using them to determine the wavelengths of radiation most suitable for phototherapy.

BRIEF SUMMARY

In various aspects, the invention relates to the use of visible electromagnetic radiation to modulate NO production and to reduce the level or production of reactive oxygen species in hypoxia. In other aspects, the invention relates to the absorption of visible light by cytochrome c mediating the effect of electromagnetic radiation on mitochondria and that the wavelength(s) of electromagnetic radiation to use in modulating mitochondrial function are those wavelengths preferentially absorbed by cytochrome c oxidase. In preferred embodiments, accordingly, the effects of the radiation are mediated by the absorption of the visible light by cytochrome c oxidase. In other embodiments, the effects of the electromagnetic radiation (e.g., visible and near infrared radiation) are mediated by the ability of the radiation to promote the phosphorylation or conversion of cytochrome c oxidase into a form which more readily generates NO.

Accordingly, in a first aspect the invention provides a method of treating hypoxia in a tissue of a mammalian subject by exposing the hypoxic tissue of the mammal to electromagnetic radiation. Exposure to the radiation improves tissue blood flow in the hypoxic state by increasing the production of NO thereby reducing vascular resistance in the tissue. Accordingly, in one embodiment, the invention provides a method of preventing or repairing tissue damage in a hypoxic tissue by exposing the tissue to electromagnetic radiation. In related embodiments, the invention provides methods of increasing mitochondrial nitrite reductase activity or NO production in the exposed tissue by exposing the tissue to electromagnetic radiation. In some embodiments, the invention provides an in vivo or in vitro method of modulating NO production by neurons or endothelial cells in a mammalian tissue capable of producing NO under hypoxic conditions and/or high concentrations of glucose by cyctochrome c nitrite reductase activity by exposing the neurons or endothelial cells to the radiation. In another embodiment, the invention relates to combination therapy of electromagnetic radiation with a second agent (e.g., nitrite, NO donors, nitroglycerin, organic nitrites, arginine) which promotes NO activity in reducing vascular resistance. In preferred embodiments, of any of the above, the radiation is in the visible portion of the electromagnetic radiation spectrum.

In a second aspect, the invention provides a method of improving energy metabolism in a hypoxic tissue by exposing the tissue to electromagnetic radiation. The exposure to electromagnetic radiation alters cytochrome c oxidase or the phosphorylation of cytochrome c oxidase in such a way as to modulate its nitrite reductase activity. Additionally, the electromagnetic radiation exposure leads to the increased expression of mitochondrial proteins leading to an increase in mitochondrial biogenesis in the tissue. In some related embodiments, the invention provides a method of modulating respiration mediated by cytochrome c oxidase in a cell of a tissue or of modulating the phosphorylation of cytochrome c oxidase in a cell of a tissue by exposing the tissue to electromagnetic radiation. In some embodiments, the amount or expression of one or more subunits selected from the group of subunits of cytochrome c oxidase, cytochrome c, cytochrome c reductase or ATP synthetase in the tissue is increased.

In a third aspect, the invention provides a method of reducing oxidative stress or toxic stress in a tissue of a mammal by exposing the tissue to electromagnetic radiation. In some embodiments, there is a reduction in any one or more of induced oxidative stress genes, levels of lipid peroxides, oxidized nucleosides and oxidized amino acids or polypeptides in the tissue. In some embodiments, the toxic stress is caused by exposure to a chemical which is metabolized to a reactive species or to generate an oxygen radical.

In a fourth aspect, the invention provides a method of monitoring the effect of treatment with electromagnetic radiation on a mammalian subject, said method comprising exposing a tissue of the subject to electromagnetic radiation and measuring the effect of the radiation on the production of NO on NO-induced vasodilators by the tissue.

In a fifth aspect, the invention provides a method of prognosis and/or diagnosis for poor blood circulation or diabetic peripheral neuropathy (DPN) in a tissue or organ, said method comprising measuring the tissue or blood NO, VEGF, or protein carbonylation levels. In some embodiments, the NO and VEGF levels indicate early stage DPN prior to loss of sensation and pain.

In a sixth aspect, the invention provides a method of treating a mammalian subject for diabetic peripheral neuropathy, said method comprising exposing an affected tissue to electromagnetic radiation.

In a seventh aspect, the invention provides a method of monitoring the response to exposure of a tissue to electromagnetic radiation by measuring blood flow in the tissue, or measuring the tissue or blood NO, VEGF, or protein carbonylation levels. In some embodiments, the response is a response according to a method of any of aspects one through six above.

In some aspects, the invention provides methods of reducing ROS in a tissue by exposing the tissue to electromagnetic radiation.

In some aspects, the invention provides methods of improved control of hyperglycemia or blood glucose levels in diabetes patients by exposing the subject to electromagnetic radiation. In some aspects, the invention provides methods of treating a neurodegenerative condition or a peripheral neuropathy by exposing the subject to electromagnetic radiation in the visible radiation range.

In some embodiments, the invention provides methods for treating diseases or conditions which may be exacerbated or caused by hypoxia or oxidative stress. Such disease or conditions include neurological/degenerative disease such as Alzheimer's disease, stroke, non-diabetic peripheral neuropathies and dementias; macular degeneration; ischemia/reperfusion disease; tissue injury; cardiovascular diseases including atherosclerosis and hypertension, diabetes and diabetic complications of the eye (e.g., macular degeneration), kidney, and nerves (e.g., diabetic peripheral neuropathy); inflammation, arthritis, radiation injury, aging, burns/wound healing; spine/back disease such as herniated discs; peripheral vascular disease, and vasospasm. In some embodiments, the invention also provides methods for treating obesity.

In some embodiments of each of the above aspects and embodiments, the wavelength of electromagnetic radiation or light to be used is visible radiation. Accordingly, in such embodiment, the wavelength of electromagnetic radiation light to be used comprises wavelengths from about 500 to 650 nm, from 550 to 625 nm, from 575 nm to about 625 nm in wavelength, or from 500 to 600 nm, 550 to 600 nm, from 575 to 600 nm. In some further embodiments of the above, the wavelength of electromagnetic radiation to be used is substantially free of light having a wavelength greater than 595 nm, 600 nm, 610 nm, 615 nm, 625 nm, 630 nm, 650 nm, or 675 nm. In yet other embodiments, the applied electromagnetic radiation is substantially free of radiation in the 615 to 750 nm range, the 620 to 700 nm range, the 630 to 700 nm range, the 630 to 750 nm range, the 630 to 675 nm range, the 650 to 700 nm range, or the 625 to 800 nm range.

In some embodiments, the wavelengths of light used fall within or are principally comprised of wavelengths falling within the primary band of mitochondrial cytochrome c oxidase. In some embodiments, the wavelengths of light used fall within the band of such wavelengths stimulating production of NO by cytochrome c oxide. In some embodiments, the light or radiation specifically targets the haem absorption bands of cyctochrome c oxidase. In further embodiments of such, the wavelengths of light are free or substantially free of wavelengths which inhibit the product of NO by cytochrome c oxidase. The period and/or intensity of this light can be adjusted to fit the individual subject or therapeutic objective as described further herein.

In some embodiments of any of the above, there is a proviso that the mammalian subject does not have diabetes. In some embodiments of any of the above, there is a proviso that the tissue is not diabetic or is not affected by DPN.

The above methods can stimulate NO production in treated tissue. Accordingly, in a further aspect of any of the above, the invention further provides for a combination therapy comprising use of any one of the above methods in combination with therapy to modulate NO activity in the subject. This therapy may include administration of NO donors and other compounds (substrates for NO synthetase, inhibitors of NO degradative pathways) which modulate NO levels in a subject.

DETAILED DESCRIPTION

The invention relates to the use of electromagnetic radiation in the visible portion of the spectrum to modulate cytochrome c oxidase, cytochrome c oxidase phosphorylation and, also, particularly, to modulate the ability of mitochondria to make NO, and additionally, the ability of this NO to modulate circulation in a tissue exposed to the electromagnetic radiation. The mitochondrion, and more particularly, cytochrome c oxidase is a major control point for cell energy production (Poyton, 1988). Accordingly, TER modulation of cytochrome c oxidase and mitochondrial function can also produce signal molecules that provide immediate benefits to cell and tissue function in hypoxic tissue. Additionally, electromagnetic radiation in the visible portion of the spectrum is useful in modulating cell viability or reproduction in hypoxic tissue and protecting cells and tissues from hypoxia. Whereas the former effects should have immediate short-term effects on cell and tissue physiology the latter effects would be expected to have more long-term effects.

Figure 1:
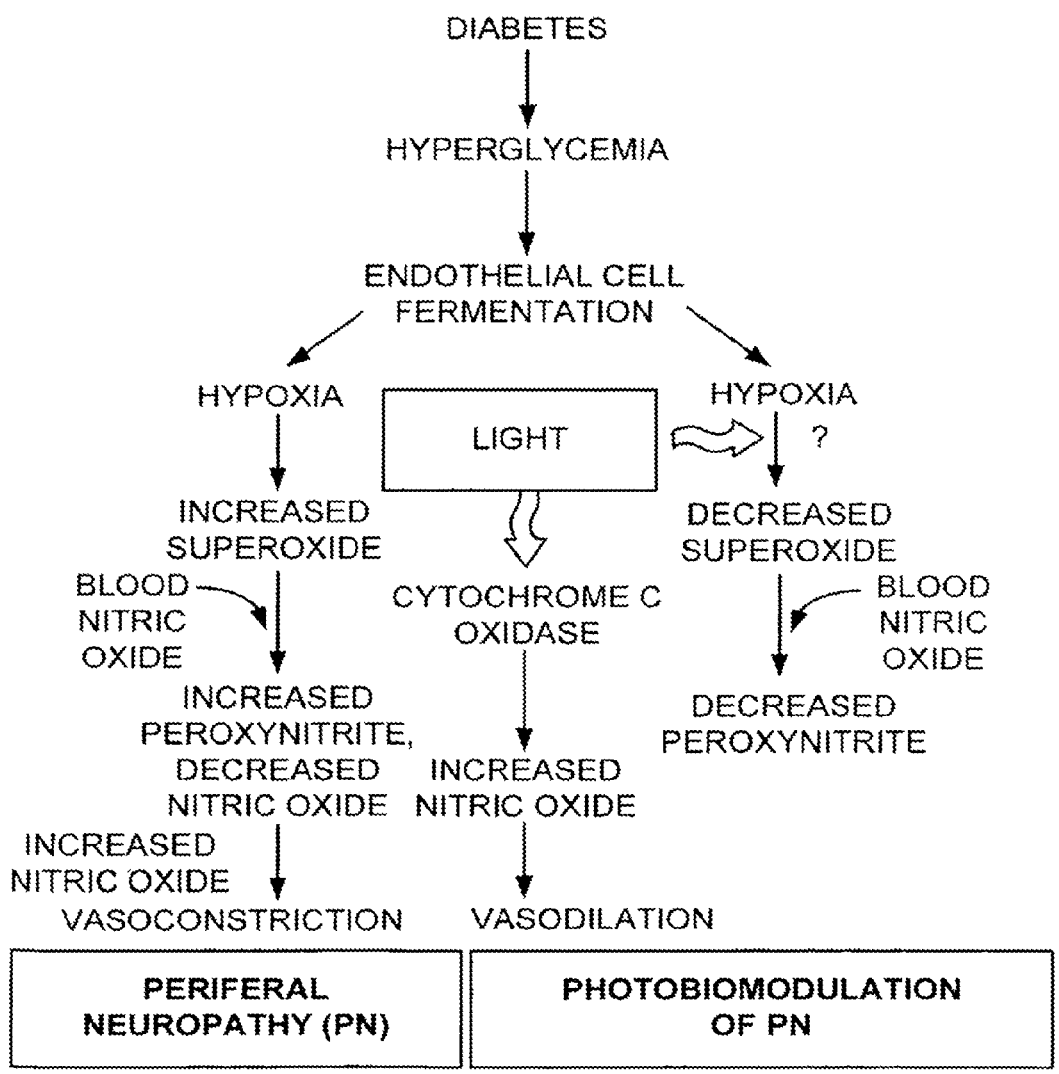
FIG. 1. Model relationships between hyperglycemia, hypoxia, vasoconstriction and photobiomodulation. Elements of this model are as follows: (1) the increased blood glucose levels in diabetes patients promotes endothelial cell aerobic fermentation reactions which promote hypoxia. (2) Under hypoxic conditions the levels of reactive oxygen species, especially superoxide, increase. (3) This superoxide reacts with NO in the blood to produce peroxynitrite. (4) The production of peroxynitrite from blood NO effectively reduces the concentration of NO in the blood, and results in protein nitration. (5) Because NO is a vasodilator reduction in blood NO levels results in the constriction of blood vessels (especially microvasculature).

The term "modulate" means to decrease or increase. The modulatory stimulus may be dynamic (varying over time) during application or constant. The visible light modulation of mitochondrial function is illustrated in FIG. 1. The modulation can be therapeutic in nature and result in the treatment (e.g., amelioration, reduction (as to either frequency or severity) or prevention (e.g., delay in onset or failure to develop) of the recited adverse condition or the signs, symptoms, or adverse sequelae of the recited adverse condition. Modulation can also promote the health of a tissue or subject with respect to a particular condition.

Much previous research has focused on the effect of light on mitochondria under conditions of normal oxygen tension. The results of these studies have indicated that Near Infrared Radiation was particularly suitable for protecting mitochondrial function. The present invention relates to the surprising finding that 1) anoxic mitochondrion also produce ATP with nitrite as an electron acceptor; 2) that light in the visible portion of the spectrum promotes the production of NO by mitochondria under these conditions; and 3) that light in the NIR which promotes ATP function in mitochondria under normal oxygen tension actually inhibits the ability of mitochondria to produce NO. As NO is a potent vasodilator, the switch to NO production is beneficial in helping restore blood flow and normal oxygen tension to hypoxic or anoxic tissue. Accordingly, the Applicants' discoveries provide new methods for treating a number of conditions where increased NO production or enhanced blood flow would be beneficial.

More particularly, the invention relates to the Applicants' discovery that visible light falling within the wavelength range of 550 to 625 nm benefits mitochondrial function under anoxic conditions and that light within a wavelength range of about 625 nm to 750 nm inhibits this therapeutic effect. Accordingly, the invention provides for improved methods of promoting mitochondrial function under conditions of reduced oxygen by applying to a target tissue monochromatic or polychromatic light of a wavelength from about 550 nm to 625 nm which is substantially free of electromagnetic radiation having longer wavelengths or free of radiation having a wavelength from about 630 nm to 700 nm in wavelength.

Accordingly, in one aspect, the invention provides methods of treating hypoxia in a tissue of a mammalian subject, said method comprising exposing the hypoxic tissue of the mammal to electromagnetic radiation in the form of visible light. In some embodiments, the response to the treatment is assessed by measuring the blood flow of the affected tissue. In other embodiments, blood or tissue levels of NO or an NO-induced vasodilator or VEGF are monitored to assess the response to the treatment. In preferred embodiments, the radiation increases NO production by mitochondria of the exposed tissue, and blood flow in the exposed tissue increases. In other embodiments, mitochondrial oxygen efficiency in the exposed tissue is increased by the exposure. In some embodiments, the hypoxia is due to poor circulation of the extremities. In exemplary embodiments, tissue is that of a subject with diabetes. In other embodiments, the treatment alleviates a sign or symptom of peripheral neuropathy in diabetic or non-diabetic patients or in patients with normal glucose control. In some embodiments of such, the treatment alleviates sensory disturbances (e.g., pin and needle sensation, numbness, burning, or other unpleasant sensations) in the extremities (e.g., feet or hands).

In another aspect, the invention provides a method of treating a mammalian subject for diabetic peripheral neuropathy by exposing an affected tissue of the subject to electromagnetic radiation in the visible portion of the spectrum. In yet another aspect, the invention provides a method of improving energy metabolism in a hypoxic tissue by exposing the tissue to this radiation. In still another aspect, the invention provides a method of reducing oxidative stress in a tissue of a mammal by exposing the tissue to electromagnetic radiation in the visible portion of the spectrum. In some embodiments of any of the above, there is a reduction in any one or more of induced oxidative stress genes, levels of lipid peroxides, oxidized nucleosides and oxidized amino acids or polypeptides in the tissue.

In a further aspect, the invention provides a method of modulating respiration mediated by cytochrome c oxidase in a cell of a tissue or of modulating the phosphorylation of cytochrome c oxidase in a cell of a tissue by exposing the tissue to electromagnetic radiation in the visible portion of the spectrum. In another aspect, the invention provides a method of modulating mitochondrial function in a tissue, said method comprising exposing the tissue to electromagnetic radiation in the visible portion of the spectrum.

In some embodiments of any of the above aspects, there are further embodiments in which the modulation increases mitochondrial nitrite reductase activity, NO production in the exposed tissue or mitochondrial biogenesis, including, for instance, the amount or expression of mitochondrial proteins. In some further embodiments, the amount or expression of one or more subunits selected from the group of subunits of cytochrome c oxidase, cytochrome c, cytochrome c reductase or ATP synthetase is increased. In some embodiments of any of the above, the radiation is visible or near-infrared radiation.

In other aspects, the invention provides a method of monitoring the effect of treatment with electromagnetic radiation in the visible portion of the spectrum on a mammalian subject, by exposing a tissue of the subject to the radiation and measuring the effect of the radiation on the production of NO on NO-induced vasodilators in the tissue.

In another aspect, the invention provides an in vivo or in vitro method of modulating NO production by cells (e.g., neurons or endothelial cells) in a mammalian tissue capable of producing NO under hypoxic conditions and/or high concentrations of glucose by cyctochrome c nitrite reductase activity, by exposing the neurons or endothelial cells to visible radiation. In these embodiments, a neurodegenerative condition can be treated. In some embodiments, the invention provides methods for increasing NO production and blood flow in the brain tissue of persons having or at increased risk of Alzheimer's disease. In some embodiments, the invention accordingly provides a method of reducing plaque formation by reducing APP processing in such persons. In still other embodiments, the invention provides methods of enhancing or improving cognitive function in subjects.

In any of the above aspects and embodiments, there are further embodiments in which an extremity is irradiated with the electromagnetic radiation in the visible portion of the spectrum. For instance, the extremity in some embodiments is the foot or hand, or lower limb. Also, in any of the above embodiments, there are embodiments in which the tissue can be a tissue of the central nervous system. In some embodiments, the tissue is a brain tissue or spinal cord tissue.

The phrase "electromagnetic radiation in the visible portion of the spectrum" comprises light having wavelengths of about 500 to 650 nm, from 550 to 625 nm, from 575 nm to about 625 nm in wavelength, or from 500 to 600 nm, 550 to 600 nm, and from 575 to 600 nm. In some embodiments, the wavelength of electromagnetic radiation to be used is substantially free of light having a wavelength greater than 600 nm, 610 nm, 615 nm 625 nm, 630 nm, 650 nm, or 675 nm. In some embodiments, the electromagnetic radiation is substantially free of radiation of inhibitory wavelengths of light or is substantially free of light in the 615 to 750 nm range, the 620 to 700 nm range, the 630 to 700 nm range, the 630 to 750 nm range, the 630 to 675 nm range, the 650 to 700 nm range, the 625 to 800 nm range. Light which is "substantially free" of certain wavelengths is light which comprises a small proportion (e.g., less that 25%, 20%, 15%, 10%, 5%, or 1%) of its total energy at the specified wavelengths) or which has a ratio of light energy in the therapeutic range (e.g., 550 nm to 625 nm) which is at least 3-fold, 4-fold, 5-fold or 10-fold greater than that of those wavelengths which inhibit the effect of the therapeutic light on the mitochondria as measured according to stimulation of NO production under anoxic conditions (e.g., inhibitory wavelengths). In some embodiments, radiation specifically targets the haem absorption bands of cyctochrome c oxidase.

In some embodiments, the wavelength of electromagnetic radiation to be used is principally composed of polychromatic light falling within the above wavelength ranges. By "principally composed," it is meant that at least 70%, 80%, 90%, or 95% of the energy of the applied light falls within the above wavelength ranges. In some embodiments, the monochromatic or polychromatic electromagnetic radiation is substantially free of radiation having wavelengths in the 615 to 750 nm range, the 620 to 700 nm range, the 630 to 700 nm range, the 630 to 750 nm range, the 630 to 675 nm range, the 650 to 700 nm range, or the 625 to 800 nm range. In further embodiments, the method employs light filters to remove one or more wavelengths of light having a wavelength from 625 to 700 nm from a polychromatic light source before the radiation from the light source is to be applied to the skin. In further embodiments of any of the above, the electromagnetic radiation in the visible portion of the spectrum is applied at a level of about 0.5 to 40, 1 to 20, or 2 to 10 joules/$cm^2$ per treatment. In some embodiments, the radiation is modulated to provide pulses of the light at a pulse frequency of 4 to 10,000 Hz.

In some embodiments of each of the above aspects and embodiments, the wavelength of visible light has a peak in the transmission spectrum from about 500 to 650 nm, from 550 to 625 nm, from 575 nm to about 625 nm in wavelength, or from 500 to 600 nm, 550 to 600 nm, from 575 to 600 nm, from 590 to 610 nm, or from 595 to 605 nm. In some further embodiments, the light has a bandwidth of about 10, 20, 30, 40, or 50 nm. In still other embodiments, the wavelength of electromagnetic radiation to be used is principally composed of one or more sources of monochromatic light within the above wavelengths. In other embodiments, the applied light can have a peak in the transmission spectrum of about 590, 591, 592, 593, 594, 595, 596, 597, 598, 599, 600, 601, 602, 603, 604, 605, 606, 607, 608, 609, 610 nm and a bandwidth of from about 5, 10, or 20 nm or less than 5, 10, or 20 nm.

The light source in any of the above embodiments can be a xenon-halogen bulb, an LED, or a laser diode.

As known to one of ordinary skill, the dosage regimen for the electromagnetic radiation in the visible portion of the spectrum can be adjusted to fit the individual subject. The period and intensity of treatment can be individualized for each subject and/or tissue. For instance, the frequency, duration, and intensity of the radiation can be adjusted according to the severity of the condition, the responsiveness of the patient, and/or according to the thickness and coloration of the skin at the point of exposure. In some embodiments of any of the above aspects, the tissue is irradiated over a treatment period of from 10 sec to 1 hour in length. In some embodiments, the treatment is given once or twice a day; 1, 2, 3, 4, or 5 times a week, or once or twice a month. In some embodiments, the treatment is given once or a few times to treat an acute condition. In other embodiments, the treatment is given on a chronic basis (lasting months to years). In yet other embodiments, the treatment may be intermittent and/or as needed to alleviate the signs and symptoms of the condition to be alleviated. Accordingly, treatments may vary in duration from the acute to the chronic. Additionally, the radiation may be applied internally (e.g., via glass fiber optics) or externally to the tissue or subject. The electromagnetic radiation in the visible portion of the spectrum is preferably not associated with any significant heating of the tissue by the energy of the radiation. In some embodiments, the radiation may be applied locally or proximal to the affected tissue or applied at a location at some distance from the affected tissue to foster a release of NO that acts upon a target tissue at a location not contacted with the applied light.

In yet another aspect the invention provides a method of prognosis and diagnosis for poor blood circulation or DPN in a tissue or organ by measuring the tissue or blood NO, VEGF, or protein carbonylation levels. In some embodiments, the NO and VEGF levels serve to indicate early stage DPN prior to loss of sensation and pain.

In another aspect, the invention provides a method of monitoring the response to exposure of a tissue to electromagnetic radiation in the visible portion of the spectrum by measuring blood flow in the tissue, or measuring the tissue or blood NO, VEGF, protein carbonylation, nitration, or nitroslylation levels in the blood or tissue. In some embodiments, this aspect can be used in evaluating the response of a tissue or subject exposed to radiation according to any of the other aspects and embodiments of the invention. Accordingly, in some embodiments, the monitoring is used to adjust the radiation treatment regimen for a tissue or subject on either an acute or chronic basis.

In one aspect the invention provides for the use of electromagnetic radiation in the visible portion of the spectrum in the therapeutic photomodulation of diabetic peripheral neuropathy. Hyperglycemia and endothelial inflammation are thought to promote a series of events that affect the vasculature that may induce DPN. Several recent studies have proposed that reactive oxygen species play a key role in many of these processes and that vascular constriction, reduced blood flow to extremities, hyperglycemia, endoneural hypoxia, nitrosative stress, and oxidative stress may all contribute to the peripheral neuropathies associated with diabetes (Pop-Busai et al. 2006). Methods and instrumentation of providing electromagnetic radiation in the visible portion of the spectrum for use according to the invention (see U.S. patent application Ser. No. 11/331,490, assigned to a same assignee as the present application and incorporated by reference herein in its entirety and particularly with respect to such methods and instrumentation) are well known to persons of ordinary skill in the art as are methods of identifying hypoxic tissues, poor blood circulation, hyperglycemia, peripheral neuropathies, and type II diabetes. In some embodiments, light emitting diode (LEDs) arrays or low energy lasers, are contemplated as sources of the radiation. Accordingly, the applied radiation can be coherent or non-coherent.

DEFINITIONS

It is noted here that as used in this specification and the appended claims, the singular forms "a," "an," and "the" include plural reference unless the context clearly dictates otherwise. As such, the terms "a" (or "an"), "one or more", and "at least one" can be used interchangeably herein.

The term "modulate" means to decrease or increase. The modulatory stimulus may be dynamic (varying over time) during application or constant. The visible light modulation of mitochondrial function is illustrated in FIG. 1. The modulation can be therapeutic in nature and result in the treatment (e.g., amelioration, reduction (as to either frequency or severity) or prevention (e.g., delay in onset or failure to develop) of the recited adverse condition or the signs, symptoms, or adverse sequelae of the recited adverse condition. Modulation can also promote the health of a tissue or subject with respect to a particular condition.

The phrase "electromagnetic radiation in the visible portion of the spectrum" comprises light having wavelengths of about 500 to 650 nm, from 550 to 625 nm, from 575 nm to about 625 nm in wavelength, or from 500 to 600 nm, 550 to 600 nm, from 575 to 600 nm. In some embodiments, the wavelength of electromagnetic radiation to be used is substantially free of light having a wavelength greater than 600 nm, 610 nm, 615 nm 625 nm, 630 nm, 650 nm, or 675 nm. In some embodiments, the electromagnetic radiation is substantially free of radiation of inhibitory wavelengths of light or is substantially free of light in the 615 to 750 nm range, the 620 to 700 nm range, the 630 to 700 nm range, the 630 to 750 nm range, the 630 to 675 nm range, the 650 to 700 nm range, the 625 to 800 nm range. Light which is "substantially free" of certain wavelengths is light which comprises a small proportion (e.g., less that 25%, 20%, 15%, 10%, 5%, or 1%) of its total energy at the specified wavelengths) or which has a ratio of light energy in the therapeutic range (e.g., 550 nm to 625 nm) which is at least 3-fold, 4-fold, 5-fold or 10-fold greater than that of those wavelengths which inhibit the effect of the therapeutic light on the mitochondria as measured according to stimulation of NO production under anoxic conditions (e.g., inhibitory wavelengths).

Additionally, the therapeutic radiation can be applied at a level of about 0.5 to 40, 1 to 20, or 2 to 10 joules/cm$^2$ per treatment. The radiation can also be modulated to provide pulses of radiation at a pulse frequency of 4 to 10,000 Hz. For instance, in some embodiments, visible radiation is applied as an intensity per treatment of 0.5 to 40 joules per treatment period and is modulated at a frequency of from 4 to 10,000 Hz. The treatments can be of varying duration (e.g., ranging from 1 to 5 minutes to an hour or more). For instance, a treatment can last for 5 to 10 minutes, 5 to 20 minutes or 20 to 40 minutes.

Accordingly, the light source used to apply the light preferably generates light in the visible range. In some embodiments of each of the above aspects and embodiments, the wavelength of electromagnetic radiation light to be used comprises wavelengths from about 500 to 650 nm, from 550 to 625 nm, from 575 nm to about 625 nm in wavelength, or from 500 to 600 nm, 550 to 600 nm, from 575 to 600 nm. In some embodiments, the wavelength of electromagnetic radiation to be used is substantially free of light having a wavelength greater than 600 nm, 610 nm, 615 nm 625 nm, 630 nm, 650 nm, or 675 nm. In some embodiments, the electromagnetic radiation is substantially free of radiation in the 615 to 750 nm range, the 620 to 700 nm range, the 630 to 700 nm range, the 630 to 750 nm range, the 630 to 675 nm range, the 650 to 700 nm range, or the 625 to 800 nm range.

In certain embodiments, the light source comprises one or more laser diodes, which each provide coherent light. In embodiments in which the light from the light source is coherent, the emitted light may produce "speckling" due to coherent interference of the light. This speckling comprises intensity spikes which are created by constructive interference and can occur in proximity to the target tissue being treated. For example, while the average power density may be approximately 10 mW/cm$^2$, the power density of one such intensity spike in proximity to the brain tissue to be treated may be approximately 300 mW/cm$^2$. In certain embodiments, this increased power density due to speckling can improve the efficacy of treatments using coherent light over those using incoherent light for illumination of deeper tissues.

In other embodiments, the light source provides incoherent light. Exemplary light sources of incoherent light include, but are not limited to, incandescent lamps or light-emitting diodes. A heat sink can be used with the light source (for either coherent or incoherent sources) to remove heat from the light source and to inhibit temperature increases at the scalp. In certain embodiments, the light source generates light which is substantially monochromatic (i.e., light having one wavelength, or light having a narrow band of wavelengths).

In further embodiments of the above, the light source generates or provides light having a plurality of wavelengths, but with the proviso that the light is substantially free of light having wavelengths ranging from 650 to 750 nm. In some embodiments, one or more optical filters are used to remove a portion of light having a wavelength falling between 625 and 750 nm.

The light source is capable of emitting light energy at a power sufficient to achieve a predetermined power density at the subdermal target tissue (e.g., at a depth of approximately 2 centimeters from the dura with respect to the brain). It is presently believed that phototherapy of tissue is most effective when irradiating the target tissue with power densities of light of at least about 0.01 mW/cm$^2$ and up to about 1 W/cm$^2$. In various embodiments, the subsurface power density is at least about 0.01, 0.05, 0.1, 0.5, 1, 5, 10, 15, 20, 30, 40, 50, 60, 70, 80, or 90 mW/cm$^2$, respectively, depending on the desired clinical performance. In certain embodiments, the subsurface power density is preferably about 0.01 mW/cm$^2$ to about 100 mW/cm$^2$, more preferably about 0.01 mW/cm$^2$ to about 50 mW/cm$^2$, and most preferably about 2 mW/cm$^2$ to about 20 mW/cm$^2$. It is believed that these subsurface power densities are especially effective at producing the desired biostimulative effects on the tissue being treated. Taking into account the attenuation of energy as it propagates from the skin surface, through body tissue, bone, and fluids, to the subdermal target tissue, surface power densities preferably between about 10 mW/cm$^2$ to about 10 W/cm$^2$, or more preferably between about 100 mW/cm$^2$ to about 500 mW/cm$^2$, can typically be used to attain the selected power densities at the subdermal target tissue. To achieve such surface power densities, the light source is preferably capable of emitting light energy having a total power output of at least about 25 m to about 100 W. In various embodiments, the total power output is limited to be no more than about 30, 50, 75, 100, 150, 200, 250, 300, 400, or 500 mW, respectively. In certain embodiments, the light source comprises a plurality of sources used in combination to provide the total power output. The actual power output of the light source is preferably controllably variable. In this way, the power of the light energy emitted can be adjusted in accordance with a selected power density at the subdermal tissue being treated.

Certain embodiments utilize a light source that includes only a single laser diode that is capable of providing about 10, 20, 25, 30, 40, or 50 mW to about 100 W of total power output at the skin surface. In certain such embodiments, the laser diode can be optically coupled to the scalp via an optical fiber or can be configured to provide a sufficiently large spot size to avoid power densities which would burn or otherwise damage the skin. In other embodiments, the light source utilizes a plurality of sources (e.g., laser diodes) arranged in a grid or array that together are capable of providing at least 10, 20, 25, 30, 40, or 50 mW to about 100 W of total power output at the skin surface. The light source of other embodiments may also comprise sources having power capacities outside of these limits.

In certain embodiments, the light source generates light which cause eye damage if viewed by an individual. In such embodiments, the light source apparatus can be configured to provide eye protection so as to avoid viewing of the light by individuals. For example, opaque materials can be appropriately placed to block the light from being viewed directly. In addition, interlocks can be provided so that the light source apparatus is not activated unless the protective elements are in place, or other appropriate safety measures are taken.

In still other embodiments, the therapy apparatus for delivering the light energy includes a handheld probe.

In certain embodiments, the application of the light is controlled by a programmable controller comprising a logic circuit, a clock coupled to the logic circuit, and an interface coupled to the logic circuit. The clock of certain embodiments provides a timing signal to the logic circuit so that the logic circuit can monitor and control timing intervals of the applied light. Examples of timing intervals include, but are not limited to, total treatment times, pulse width times for pulses of applied light, and time intervals between pulses of applied light. In certain embodiments, the light sources can be selectively turned on and off to reduce the thermal load on the skin and to deliver a selected power density to particular areas of the brain or other target tissue/organ.

In some embodiments, the applied light source is controlled by a logic circuit coupled to an interface. The interface can comprise a user interface or an interface to a sensor monitoring at least one parameter of the treatment. In certain such embodiments, the programmable controller is responsive to signals from the sensor to preferably adjust the treatment parameters to optimize the measured response. The programmable controller can thus provide closed-loop monitoring and adjustment of various treatment parameters to optimize the phototherapy. The signals provided by the interface from a user are indicative of parameters that may include, but are not limited to, patient characteristics (e.g., skin type, fat percentage), selected applied power densities, target time intervals, and power density/timing profiles for the applied light.

In certain embodiments, the logic circuit is coupled to a light source driver. The light source driver is coupled to a power supply, which in certain embodiments comprises a battery and in other embodiments comprises an alternating current source. The light source driver is also coupled to the light source. The logic circuit is responsive to the signal from the clock and to user input from the user interface to transmit a control signal to the light source driver. In response to the control signal from the logic circuit, the light source driver adjusts and controls the power applied to the light sources.

In certain embodiments, the logic circuit is responsive to signals from a sensor monitoring at least one parameter of the treatment to control the applied light. For example, certain embodiments comprise a temperature sensor thermally coupled to the skin to provide information regarding the temperature of the skin to the logic circuit. In such embodiments, the logic circuit is responsive to the information from the temperature sensor to transmit a control signal to the light source driver so as to adjust the parameters of the applied light to maintain the scalp temperature below a predetermined level. Other embodiments include exemplary biomedical sensors including, but not limited to, a blood flow sensor, a blood gas (e.g., oxygenation) sensor, an NO production sensor, or a cellular activity sensor. Such biomedical sensors can provide real-time feedback information to the logic circuit. In certain such embodiments, the logic circuit is responsive to signals from the sensors to preferably adjust the parameters of the applied light to optimize the measured response. The logic circuit can thus provide closed-loop monitoring and adjustment of various parameters of the applied light to optimize the phototherapy.

Preferred methods of phototherapy for a selected wavelength(s) are based upon recognition that the power density (light intensity or power per unit area, in W/cm$^2$) or the energy density (energy per unit area, in J/cm$^2$, or power density multiplied by the exposure time) of the light energy delivered to tissue is an important factor in determining the relative efficacy of the phototherapy.

In certain embodiments, the light source can be adjusted to irradiate different portions of the subject's skin or scalp in order to target underlying brain tissue which, for instance, has been the subject of a pathology or neurodegeneration.

As used herein, the term "neurodegeneration" refers to the process of cell destruction or loss of function resulting from primary destructive events such as stroke or CVA, as well as from secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amyotrophic lateral sclerosis, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. In some embodiments, the methods according to the invention can be used to treat Huntington's disease; Parkinson's disease; familial Parkinson's disease; Alzheimer's disease; familial Alzheimer's disease; amyotrophic lateral sclerosis; sporadic amyotrophic lateral sclerosis; mitochondrial encephalomyopathy with lactic acidosis and strokelike episodes; myoclonus epilepsy with ragged-red fibers; Kearns-Sayre syndrome; progressive external ophthalmoplegia; Leber hereditary optic neuropathy (LHON); Leigh syndrome; and Friedreich ataxia, and cytochrome c oxidase (CCO) deficiency states.

As used herein, the term "neuroprotection" refers to a therapeutic strategy for slowing or preventing the otherwise irreversible loss of neurons or CNS function due to neurodegeneration after a primary destructive event, whether the neurodegeneration loss is due to disease mechanisms associated with the primary destructive event or secondary destructive mechanisms.

Additionally, inflammation and oxidative stress are important in the pathology of many chronic neurodegenerative conditions, including Alzheimer's disease. This disease is characterized by the accumulation of neurofibrillary tangles and senile plaques, and a widespread progressive degeneration of neurons in the brain. Senile plaques are rich in amyloid precursor protein (APP) that is encoded by the APP gene located on chromosome 21. Pathogenesis of AD may be mediated by an abnormal proteolytic cleavage of APP which leads to an excess extracellular accumulation of beta-amyloid peptide which is toxic to neurons (Selkoe et al., (1996), J. Biol. Chem. 271:487-498; Quinn et al., (2001), Exp. Neurol. 168:203-212; Mattson et al., (1997), Alzheimer's Dis. Rev. 12:1-14; Fakuyama et al., (1994), Brain Res. 667:269-272). Methods of assessing neuroprotection are well known in the art (see, for instance, U.S. Patent publication no. 20080107603 and U.S. Pat. No. 6,803,233 which are incorporated herein by reference). A beneficial outcome of light dependent CCO NO production is the nitrosylation and subsequent down regulation of gamma secretase activity. The decreased gamma secretase activity would in turn decrease the production of harmful beta amyloid peptides.

Accordingly, in some embodiments, an object of the present invention is to provide a treatment of dementia which can ameliorate learning and/or memory impairments, or cognitive impairment in Alzheimer's-type dementia, cerebrovascular dementia and senile dementia.

In some embodiments, the invention provides a method of treating a subject having a disorder involving impaired mitochondrial function. Generally, the method includes administering a phototherapy of the present invention to such a subject under conditions effective to improve mitochondrial function. This method of the present invention is particularly useful for the treatment or prophylaxis of disorders associated with impaired mitochondrial function. Disorders that can be treated according to this method generally include conditions or diseases characterized by a decreased level of oxidative metabolism. The disorders may be caused by genetic factors, environmental factors, or both. More specifically, such disorders include conditions or diseases of the nervous system (e.g., neurodegenerative, psychoses, etc.), conditions or diseases of other parts of the body, and conditions or diseases of the body as a whole. Such conditions or diseases of the nervous system include not only Alzheimer's Disease, Parkinson's Disease, Huntington's Disease, but also spinocerebellar ataxias, and psychoses (including depression or schizophrenia) associated with oxidative metabolic abnormalities. Exemplary conditions or disorders of other parts of the body include cardiovascular disorders (e.g., atherosclerotic and cardiovascular diseases including myocardial infarctions, angina, cardiomyopathies, cardiac valvular disorders, and other conditions or disorders causing cardiac failure), musculoskeletal disorders in which oxidative metabolism is abnormal and other conditions or disorders of non-neural tissues in which oxidative metabolism is abnormal, such as frailty, a geriatric syndrome often associated with metabolic alterations.

Many conditions or diseases of the nervous system (e.g., AD and those described above) are characterized by cerebral metabolic insufficiencies, which are manifested as impaired cerebral function such as dementia. Therefore, another aspect of the present invention relates to a method of improving cerebral function in a subject having cerebral metabolic insufficiencies. Generally, a pharmaceutical composition of the present invention is administered to a subject having impaired cerebral metabolism under conditions effective to improve the cerebral cellular metabolism. By improving cerebral cellular metabolism, the subject's cerebral function is improved significantly The terms "treating" or "treatment" refer to therapeutic methods involving the application of an agent which benefits a particular disease or condition. For instance, a phototherapy according to the invention can be used to slow the progression or onset of the disease or condition, and/or to reduce the signs and/or symptoms or physical manifestations of the disease or condition. A therapeutically effective amount of an agent references a quantity or dose of an agent (e.g., radiation or drug) which is sufficient to treat the disease or condition. Many models systems for determining the efficacy of neuroprotective agents are known in the art. Such model systems can be used to assess the efficacy of treatments according to the invention. For instance, behavioral assessments as known to one of ordinary skill in the art can be used in humans or test animals for cognitive impairment. In test animals, the spatial memory test using Y-maze apparatus can be used to test the behavioral property of animals to enter into a new arm, avoiding the arm that they entered into just before (alternation behavior). (See Itoh, J., et al. (Eur. J. Pharmacol., 236, 341-345 (1993)). Alternatively or additionally, histopathological methods monitoring cell death, accumulation of neurofibrillary tangles or senile plaque can be used to assess the extent of neurodegeneration.

A neuroprotective-effective amount of light energy achieves the goal of reversing, preventing, avoiding, reducing, or eliminating neurodegeneration.

In certain embodiments, the "neuroprotection" involves treating a patient (e.g., Alzheimer's disease) by placing the therapy apparatus in contact with the scalp and adjacent the target area of the patient's brain. The target area of the patient's brain can be previously identified such as by using standard medical imaging techniques. In certain embodiments, treatment further includes calculating a surface power density at the scalp which corresponds to a preselected power density at the target area of the patient's brain. The calculation of certain embodiments includes factors that affect the penetration of the light energy and thus the power density at the target area. These factors include, but are not limited to, the thickness of the patient's skull, type of hair and hair coloration, skin coloration and pigmentation, patient's age, patient's gender, and the distance to the target area within the brain. The power density and other parameters of the applied light are then adjusted according to the results of the calculation.

The power density selected to be applied to the target area of the patient's brain depends on a number of factors, including, but not limited to, the wavelength of the applied light, the location and severity of the pathology, and the patient's clinical condition, including the extent of the affected brain area. The power density of light energy to be delivered to the target area of the patient's brain may also be adjusted to be combined with any other therapeutic agent or agents, especially pharmaceutical neuroprotective agents, to achieve the desired biological effect. In such embodiments, the selected power density can also depend on the additional therapeutic agent or agents chosen.

In preferred embodiments, the treatment proceeds continuously for a period of about 10 seconds to about 2 hours, more preferably for a period of about 1 minute to about 10 minutes, and most preferably for a period of about 2 minutes to 5 minutes. In other embodiments, the light energy is preferably delivered for at least one treatment period of at least about 5 minutes, and more preferably for at least one treatment period of at least 10 minutes. The light energy can be pulsed during the treatment period or the light energy can be continuously applied during the treatment period.

In certain embodiments, the treatment may be terminated after one treatment period, while in other embodiments, the treatment may be repeated for at least two treatment periods. The time between subsequent treatment periods is preferably at least about 5 minutes, more preferably at least about 1 to 2 days, and most preferably at least about one week. The length of treatment time and frequency of treatment periods can depend on several factors, including the functional recovery or response of the patient to the therapy.

A method for the neuroprotective treatment of a patient in need of such treatment involves delivering a neuroprotective-effective amount of light energy having a wavelength in the visible range to a target area of the patient's brain. In certain embodiments, the target area of the patient's brain includes the area of plaque accumulation or ischemia, i.e., to neurons within the "zone of danger." In other embodiments, the target area includes portions of the brain not within the zone of danger. Without being bound by theory, it is believed that irradiation of healthy tissue in proximity to the zone of danger increases the production of NO in the irradiated tissue which can improve blood flow in adjoining hypoxic tissue, including injured.

Apparatus and methods adaptable for in the application of light to the brain according to the present invention are disclosed in U.S. Patent Application Publication No. 2006/0253177 which is incorporated herein by reference.

In certain embodiments, a method provides a neuroprotective effect in a patient that has had an ischemic event in the brain. The method comprises identifying a patient who has experienced an ischemic event in the brain. The method further comprises estimating the time of the ischemic event. The method further comprises commencing administration of a neuroprotective effective amount of light energy to the brain or the affected area of the brain and/or an area proximal thereto. The administration of the light energy is commenced no less than about two hours following the time of the ischemic event. In certain embodiments, phototherapy treatment can be efficaciously performed preferably within 24 hours after the ischemic event occurs, and more preferably no earlier than two hours following the ischemic event, still more preferably no earlier than three hours following the ischemic event, and most preferably no earlier than five hours following the ischemic event. In certain embodiments, one or more of the treatment parameters can be varied depending on the amount of time that has elapsed since an ischemic event.

The invention also provides a method of treating Alzheimer's disease (e.g., slowing the progression or onset of the condition, or reducing the signs and/or symptoms or physical manifestations of the disease). Much evidence indicates that less oxygenated blood flowing to the brain contributes to the build-up of the protein plaques associated with Alzheimer's disease. Alterations in mitochondrial function, including particularly cytochrome c oxidase activity have also been reported in Alzheimer's disease patients as well. We have shown that, under hypoxic conditions, visible light can activate cytochrome c to produce nitric oxide, a potent vasodilator. Vasodilation can increase the amount oxygen available to cells as well as directly promote mitochondrial function in these patients. Accordingly, in one aspect, the invention provides phototherapy for Alzheimer's disease.

In some embodiments of the above where the brain is to be treated, the external carotid artery and or the vertebral artery are exposed to light by the application of the visible light from the sides of the head. The shortest distance to these structures is from the sides. Positioning the treatment heads or light sources directly under the ear and behind the jaw bone would give the most direct access to these structures for the radiant energy applied. In other embodiments, the vertebral artery is treated by the application of the light from the rear of the skull or from the sides of the skull.

Figure 9:
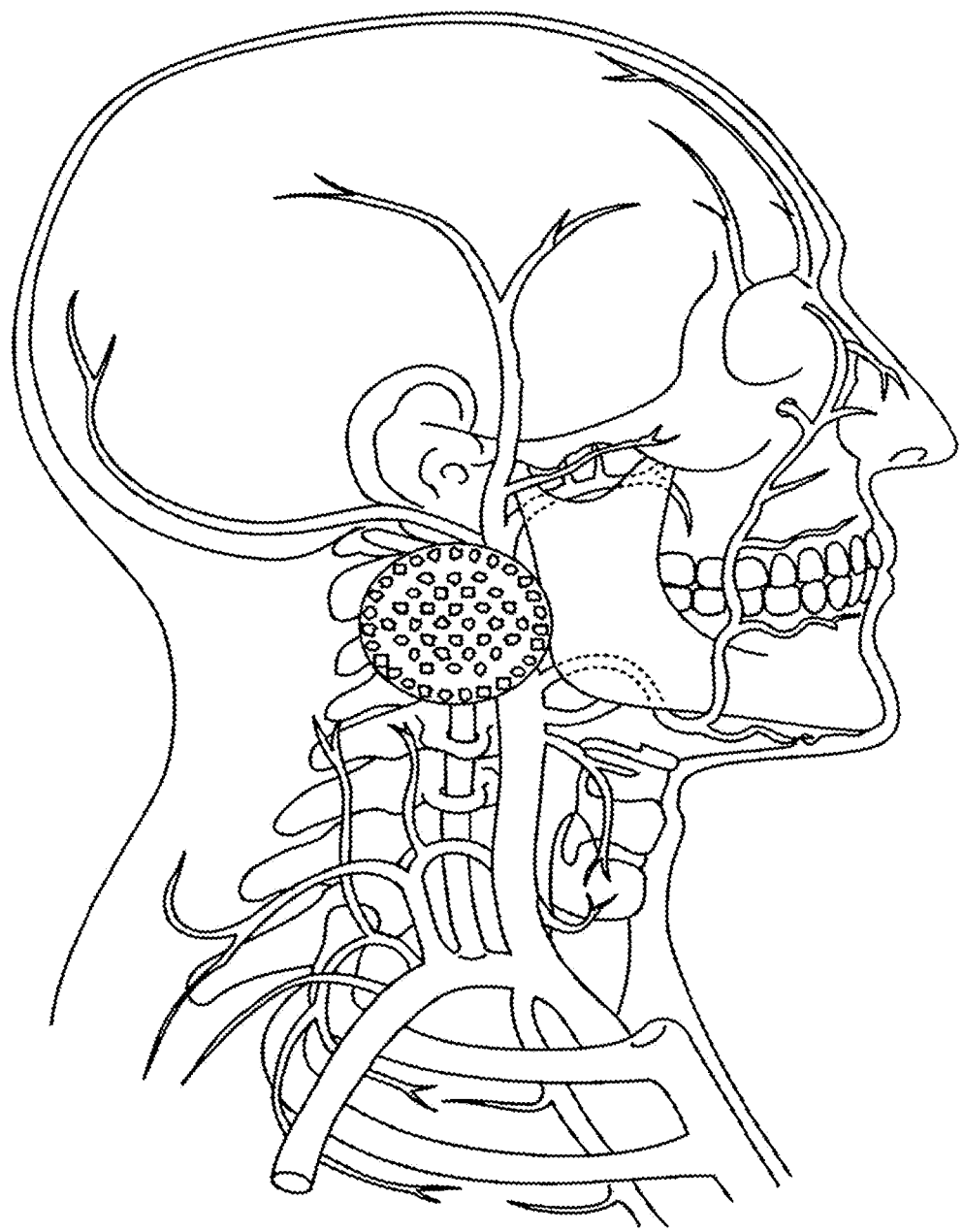
FIG. 9. Model depicting a suitable placement of a treatment head for purposes of phototherapy affecting the brain.

In some embodiments where the brain is to be treated, the treatment head should be applied to the head below the ear and just behind the jaw bone (see FIG. 9). This will maze the irradiation area of the supplying vessels to the brain due to having to traverse less soft tissue. This illustrates that a treatment head of approximately 2 inches in diameter would cover both structures. Other treatment heads may be used, including those of from 0.5 to 4 inches in diameter. The treatment heads need not be circular but can be configured so as to track the location of the targeted arteries more closely. In some embodiments, the treatment heads can have an application surface area of from about one or two square inches to 4, 8 or 10 square inches. In some embodiments, the treatments can be applied to either or both sides of the body.

In some embodiments, the effect of the treatment on Alzheimer's disease can be monitored by assessing the effect on the treatment on the disease progression itself or indirectly by monitoring biomarkers of disease progression or pathogenesis (e.g, APP and APP products, gamma secretase (including but not limited to particularly the presenilin subunit) levels; mitochondrial CCO subunit IV (mammalian, V yeast) isoforms)). (see Schon et al., J. Clin. Invest. 111(3): 303-312 (2003)).

Example 1

Role of the Respiratory Chain in NO Production in Endothelial Cells Under Hypoxic Conditions Currently, there are two known pathways for NO synthesis. The first involves nitric oxide synthase (NOS), an enzyme that converts arginine to citrulline in the presence of NADPH and oxygen. There are three isoforms of nitric oxide synthase (NOS). These are designated NOS I (neuronal NOS), NOS II (inducible NOS), and NOS III (endothelial NOS). The second pathway for NO production involves nitrite-dependent NO production by the mitochondrial respiratory chain. This pathway is active only at reduced oxygen concentrations.

The relative importance of the NOS-dependent and NOS-independent NO synthesis in endothelial cells is assessed before and after visible light treatment. The production of NO is evaluated in cells exposed to hypoxic conditions in the presence of physiological concentration of nitrite. The involvement of the respiratory chain in this process is evaluated in the presence of: a) L-NAME, a general NOS inhibitor, b) inhibitors of the respiratory chain, c) disruptors of the mitochondrial membrane potential, d) inhibitors of mitochondrial complex IV, e) inhibitors of constitutive NOS, and e) theophylline.

Example 2

NO Production by Endothelial or Cells

Endothelial cells are isolated and cultured as described elsewhere (Wang et al., 2007; Wang et al., 2004). Hypoxia (1.5% $O_2$, 93.5% $N_2$, 5% $CO^2$) or anoxia (5% $CO_2$, 4% $H_2$, 91% $N_2$) is established in an IN VIVO workstation (Biotrace) or Coy laboratories glove box, pre-equilibrated with the appropriate gas mixture. All cell extracts are prepared inside the workstation or glove box to prevent re-oxygenation. Cells are maintained under anoxic or hypoxic conditions for varying lengths of time (2-8 hr). Nitric oxide production is evaluated with the fluorescent nitric oxide indicator DAF-FM (Molecular Probes, CA). Nutrient media are supplemented with 20 µM $N_aNO_2$. The involvement of the respiratory chain in nitrite dependent NO production is evaluated in the presence of: a) the inhibitors of complex III Antimycin A (10 µM), myxothiazol (10 µM) and Cyanide (1 mM); b) disruptors of the mitochondrial membrane potential FCCP (10 µM) and dinitrophenol (100 µM); c) inhibitors of mitochondrial complex V oligomycin 10 uM; and d) L-NAME, an inhibitor of constitutive NOS L-NAME (1 mM).

Example 3

Mitochondrial Functionality and NO Production

Mitochondria from normal and hypoxic cells is isolated and evaluated for respiratory control, hypoxic production of nitrite dependent NO production, and production of nitrite dependent NO production after incubation with ATP and theophylline, using methods described previously (Castello et al., 2006).

Example 4

Stimulation of Nitrite Reductase Activity and Subunit Phosphorylation of Cytochrome C Oxidase by Visible Light The effects of visible light on the nitrite-reductase activity of cytochrome c oxidase can be assessed in isolated mitochondria and purified cytochrome c oxidase.

Nitrite-Dependent NO Production.

Initially, NO levels are measured in isolated mitochondria, using an NO meter or the fluorescent probe DAF-FM (Molecular Probes, CA). Mitochondria exposed to visible light are treated with specific respiratory inhibitors in order to localize NO production to cytochrome c oxidase, as described previously (Castello et al. 2006). Visible light stimulation of NO production in mitochondria is observed.

The effects of visible light on nitrite-dependent NO production by isolated cytochrome c oxidase, purified from both mammals and yeast is next studied.

Phosphorylation of Subunits of Cytochrome C Oxidase.

The Tyr-phosphorylation of COX is analyzed following immunoprecipitation, gel electrophoresis, and immunoblotting (Lee et al., 2005).

Example 5

Effect of Visible Light on Intracellular Levels of Oxidative Stress and/or Mitochondrial Biogenesis in Endothelial and Yeast Cells These studies examine the long-term effects of visible exposure on endothelial and yeast cells in culture. Specifically, visible exposure is found to enhance the production of new mitochondria and an increase in cellular respiratory metabolism. This result is shown by assessing the effects of visible light on cellular respiration and the intracellular levels of mitochondrial proteins, including the subunits of cytochrome c oxidase. Increased rates of cellular respiration lead to reduced generation of ROS by the mitochondrial respiratory chain. The effects of visible light on cellular respiration, oxidative stress, and mitochondrial biogenesis (i.e., the synthesis of new mitochondria) are evaluated. By changing the wavelength(s) of visible radiation used for exposure the wavelengths most effective for treating hypoxia are identified.

Example 6

Mitochondrial Hydrogen Peroxide Production

One way of assessing the effects of visible light on cellular oxidative stress is to measure the production of ROS by the respiratory chain. This is done using isolated mitochondria and an hydrogen peroxide electrode connected to a W.P.I. amplifier.

Measurement of Protein Carbonylation.

Generally speaking, three types of assay are used for assessing cellular oxidative stress. The first makes use of fluorescent dyes (e.g., derivatives of fluorescein or rhodamine) to estimate intracellular ROS levels. The second assesses oxidative damage, caused by ROS, by measuring the accumulation of lipid peroxides (e.g., malonaldehyde and hydroxyalkenals), oxidized nucleosides (e.g., 8-hydroxy-2'-deoxyguanosine (8-OHdG)), or oxidized amino acid side chains on proteins (e.g., o-tyrosine, m-tyrosine, dityrosine, and carbonyl derivatives). The third measures the expression of oxidative stress-induced genes.

Protein carbonylation is used to indicate overall levels of cellular oxidative stress. Carbonyl content of mitochondrial and cytosolic protein fractions is measured after derivatizing proteins in each fraction with 2,4-dinitrophenyl hydrazine (DNPH) as described (Dirmeier et al. 2002; 2004).

Mitochondrial Biogenesis.

In order to determine if light impacts the synthesis of new mitochondria and, consequently, the level of cellular respiration, oxygen consumption rates are measured using an oxygen electrode. Altered intracellular levels of key mitochondrial proteins (subunits of cytochrome c oxidase, cytochrome c, cytochrome c reductase, and ATP synthase) are measured after cells are exposed to light. Levels of these proteins are determined by immunoblotting SDS-gels of whole cell extracts.

Example 7

Visible Light Increases Levels of Vasodilators in the Blood

NO and VEGF are measured in venous blood and exposed tissues after patients with peripheral neuropathies are exposed to visible light. VEGF levels will be assessed by an immunoassay and NO levels will be measured with an NO meter or the fluorescent NO indicator DAF-FM.

Measurement of NO Levels in the Blood.

Venous blood will be collected from patients and frozen. Because NO is unstable and rapidly converted to nitrate in the presence of oxidized hemoglobin we will not be able to measure NO directly. Instead, we will convert nitrate to nitrite and NO chemically, using copper-coated cadmium as a reducer (NITRALYZER™-II, WPI, FL). The NO that is produced will be measured with an NO electrode connected to an NO/Free radical analyzer.

VEGF Levels.

VEGF levels in the blood will be determined after running whole blood on an SDS-polyacrylamide gel and immunoblotting the gel with an antibody specific for VEGF.

Example 8

The overall goal of this study was to examine the relationship(s) between light and cellular nitrite-dependent nitric oxide production by mitochondrial cytochrome c oxidase. The yeast *Saccharomyces cerevisiae* was used as a model for these studies. Specific Aims were to:

1) Determine if light affects nitrite-dependent nitric oxide production in yeast cells and if so, assess whether it has a stimulatory or inhibitory effect.

2) Determine the effects of light intensity on cellular nitrite-dependent nitric oxide production.

3) Identify an action spectrum for the stimulatory or inhibitory effects of light on cellular nitrite-dependent nitric oxide production.

Figure 2:
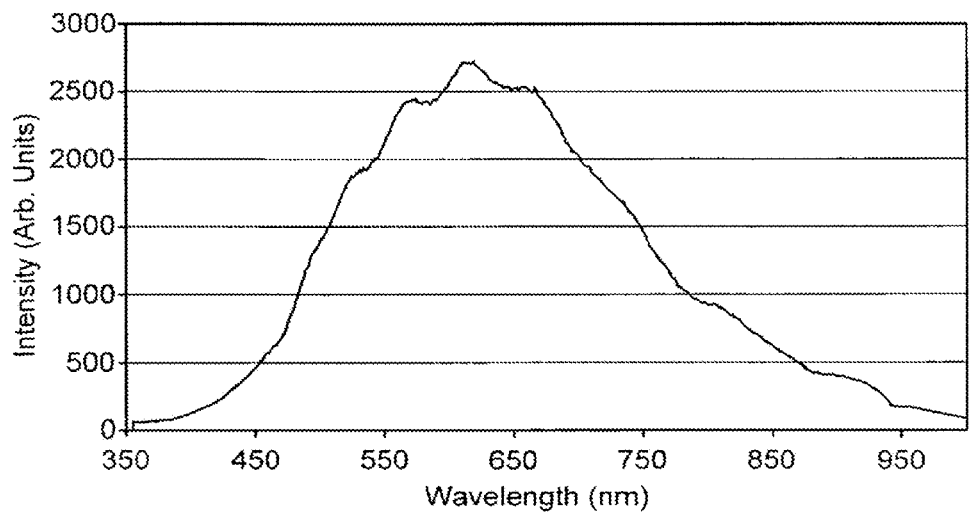
FIG. 2. Spectral emission from a 50 watt Xenon/Halogen flood light (Feit Electric Co.).

The effects of broad spectrum light on nitrite-dependent nitric oxide production by hypoxic yeast cells was examined. Initially, several experimental conditions were surveyed in order to determine the best way to assess the effects of light on cellular nitrite-dependent nitric oxide production. These included: investigating different types of light source, controlling for temperature, varying the time of addition of substrate (nitrite), and examining the time and duration of illumination. After preliminary studies with these variables we decided to use a 50 watt Xenon/Halogen flood light (Feit Electric Co.) capable of producing broad spectrum visible and near IR light. Spectral emission from this bulb (FIG. 2) was determined using an Ocean Optics Diode Array Fiber Optic spectrophotometer (Model SD 2000) by personnel in the Integrated Instrument Development Facility of CIRES lab at the University of Colorado, Boulder.

Cells being assayed were kept at a constant temperature of 28° C. in a water jacketed chamber and a heat filter was placed between the light source and the cells in order to insure that the effects observed were due to light and not a change in temperature due to illumination. Light intensity at the surface of the assay chamber was measured with a Newport Instruments 918D-SL Power meter. All studies were done in a darkened room. Cells were exposed to a light intensity of 7 $mW/cm^2$, which corresponds to setting the light bulb 20 inches from the assay chamber. The length of time cells were exposed to light was varied in order to deliver variable levels of total light energy. Prior to exposure to light the cell suspension was sparged with nitrogen gas to remove oxygen. They were then exposed to light for variable times and then nitrite was added to start the reaction. Nitric oxide levels were measured with a nitric oxide electrode attached to a WPI Apollo 4000 nitric oxide meter.

Figure 3:
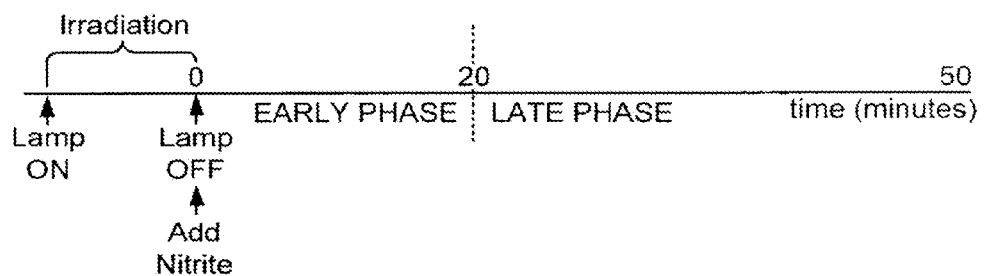
FIG. 3. Two experimental conditions tested for nitrite-dependent nitric oxide production in yeast cells.
Figure 3:
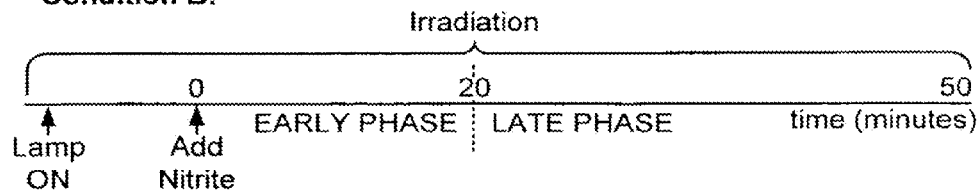
Figure 4:
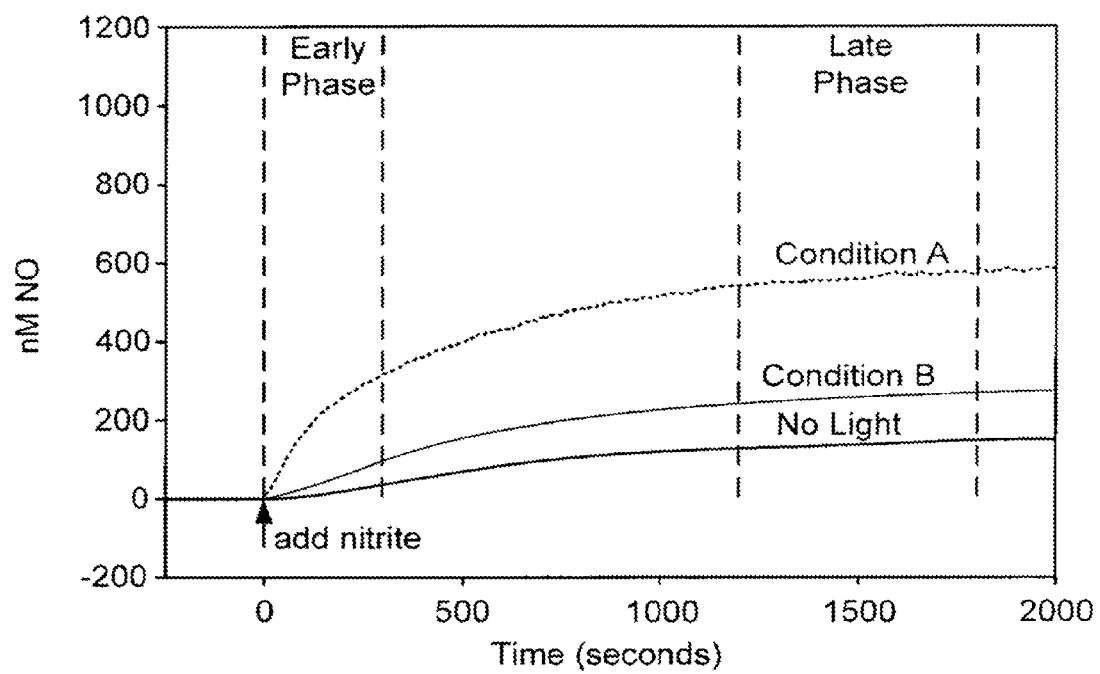
FIG. 4. Light stimulated nitrite-dependent production of NO.

As shown in FIG. 3, two experimental conditions were tested. In Condition A, cells were pre-conditioned by exposure to light for variable lengths of time, prior to the addition of nitrite. Upon addition of nitrite the light was turned off. Condition B was the same as Condition A except that the light was kept on for the duration of the experiment. The effect of broadband light on nitrite-dependent nitric oxide production under Conditions A and B is shown in FIG. 3. By comparing nitric oxide production under Conditions A and B with nitric oxide production in the absence of light it is clear that broadband light stimulates nitrite-dependent nitric oxide production in hypoxic cells under both Conditions A and B and that there are two distinct phases. The initial phase is characterized by the rapid production of nitric oxide. This phase is followed by a slower phase. For convenience, we have termed the initial phase the "early phase" and the second phase the "late phase". It is not known why the rate slows, but it is likely that the overall level of nitric oxide produced is determined largely by the enhanced rates observed during the early phase. Although either phase can be used for these studies we have observed that the late phase rates and overall levels of nitric oxide production are more reproducible than the early phase rates. From FIG. 4 it is obvious that the additional light energy received during Condition B gives less enhancement on the rate of nitric oxide production than the protocol followed in Condition A. Indeed, the pre-conditioning step with light in Condition A seems to be sufficient. Because of this, all subsequent studies have been done using Condition A.

Figure 5:
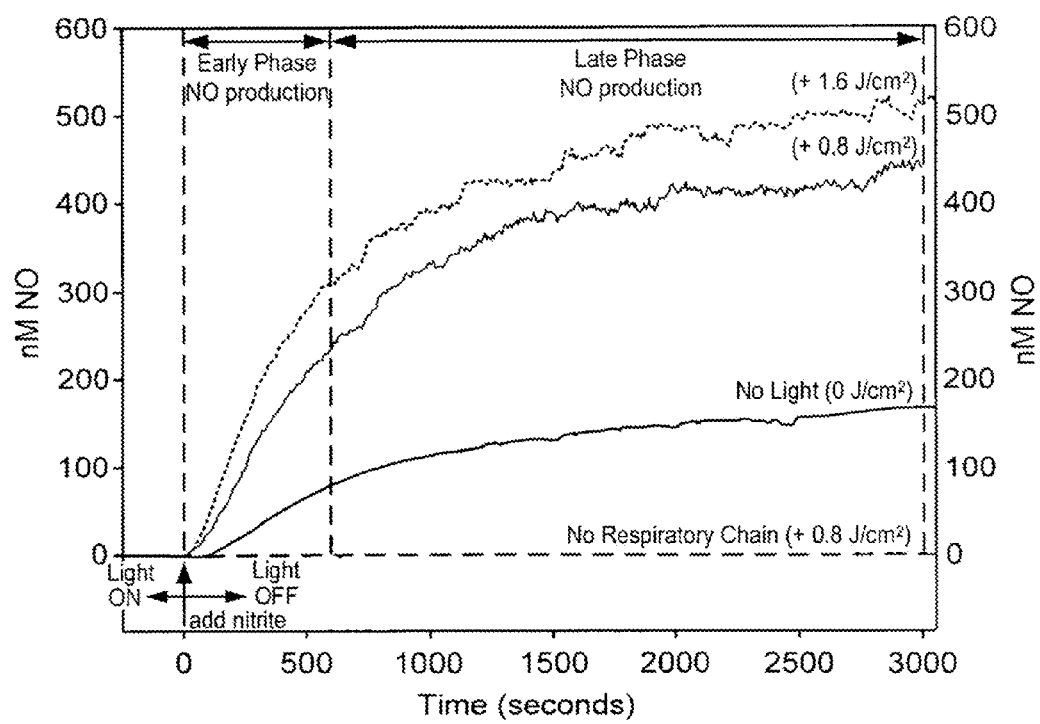
FIG. 5. Comparison of the effects of light intensity and a respiratory chain on light-stimulated nitric oxide production in yeast cells.
Figure 6:
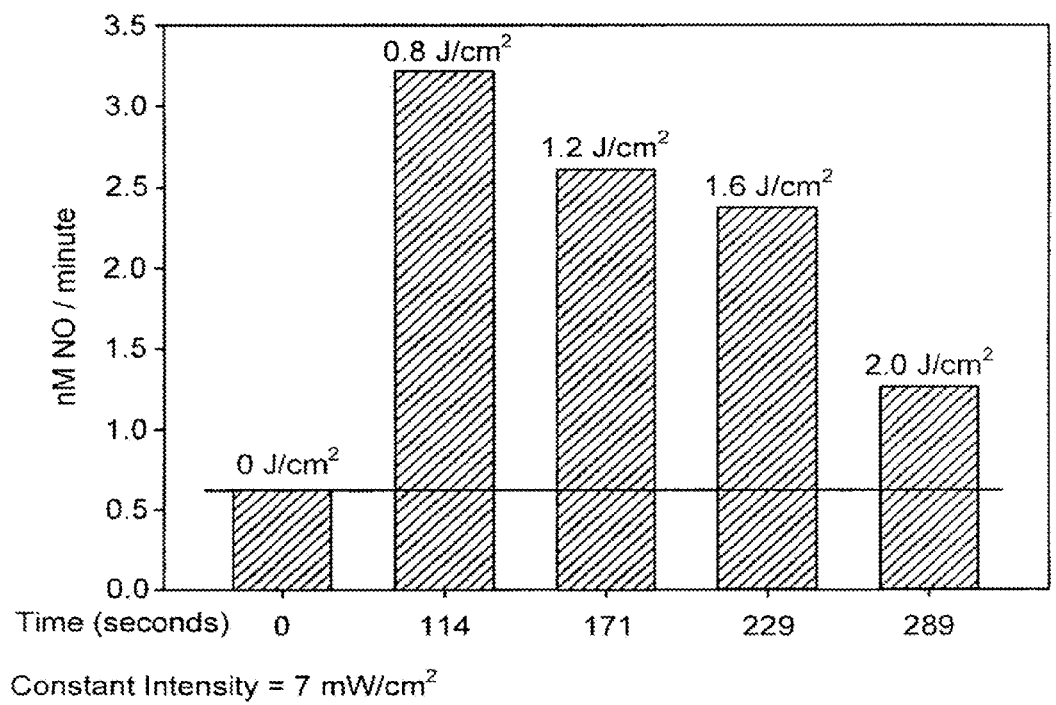
FIG. 6. Power dependence of late phase light-stimulated nitric oxide production in yeast cells.

The effect of light intensity on nitrite-dependent nitric oxide production by yeast cells was determined by varying the exposure time during the pre-conditioning phase. From FIG. 5, it is clear that the stimulatory effect of light on nitrite-dependent nitric oxide production requires the respiratory chain because it is not observed in a strain that is respiration-deficient. It is also clear that increasing light intensity from 0.8 to 1.6 $J/cm^2$ increased the early phase rate of nitric oxide production. A more complete analysis of the effects of light intensity on the rates of nitrite-dependent nitric oxide production during the late phase is shown in FIG. 6. Maximum stimulation of the rates of nitric oxide synthesis are observed at light intensities of 0.8 $J/cm^2$. A similar relationship between light intensity and nitric oxide production was observed for nitric oxide synthesis during the early phase.

Figure 7:
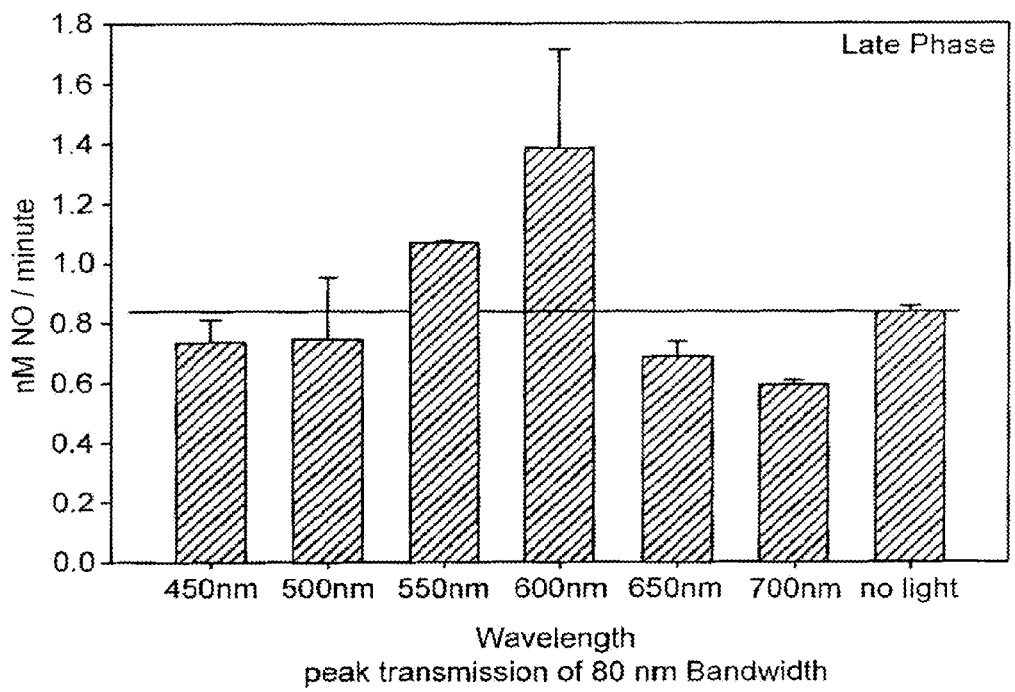
FIG. 7. Overall rates of nitric oxide production during the late phase as a function of wavelength.
Figure 8:
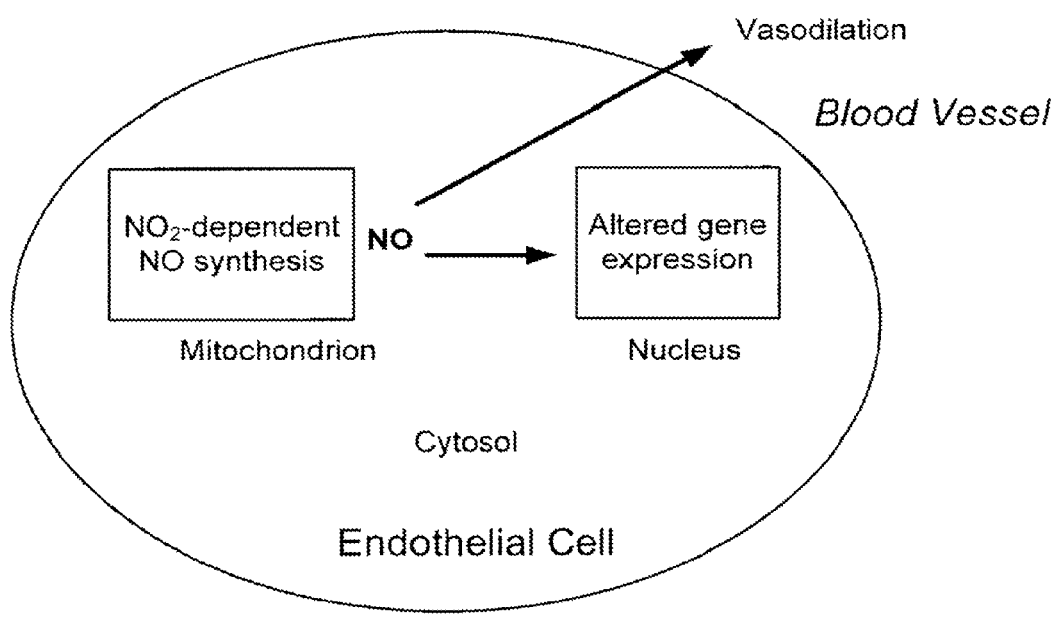
FIG. 8. Diagram depicting intracellular and extracellular actions of NO.

A series of broadband interference filters from Edmund Scientific were used to assess the effects of specific wavelengths of light on nitrite-dependent nitric oxide production and hence produce an action spectrum we used. These filters had peak transmittance every 50 nm and a full width half maximum bandwidth (FWHM) of 80 nm. The overall rates of nitric oxide production during the late phase are shown in FIG. 7. Maximum stimulation of nitric oxide production was observed when cells were stimulated with the 550±40 nm and 600±40 nm filters. Wavelengths transmitted by the 450 and 500 nm filters had no effect on nitric oxide production. Surprisingly, those wavelengths transmitted by the 650 and 700 nm filters light had an inhibitory effect on nitrite-dependent nitric oxide production when compared to the no light control. In order to further refine the wavelength dependence of both the stimulatory and inhibitory effects of light on nitrite dependent nitric oxide production we have tried to use narrow bandwidth interference filters from Cheshire optical. These filters had center wavelengths spaced every 10±2 nm and covered the range between 530 and 850 nm. Unfortunately, because these narrow band filters reduce the level of light transmission to a level that is below that required for light stimulated nitric oxide synthesis they were not suitable for establishing a higher resolution action spectrum.

The results obtained from the above studies clearly support the conclusion that broadband light affects nitrite-dependent nitric oxide production in yeast cells and does so in a dose-dependent fashion. They also support the conclusion that some wavelengths of light are stimulatory while others are inhibitory. In addition, the experiments performed during the past 3.5 months have indicated that while light bulbs can be used for these studies they suffer from the disadvantage that their output spectra change as they age. This is inconvenient and suggests that alternative sources of light energy (e.g., LEDs) will be more appropriate for future studies.

REFERENCES

Baynes, J. W. 1991. *Diabetes* 40, 401-412.
Baynes, J. W. and Thorpe, S. R. 1999. *Diabetes* 48, 1-9.
Beauvoit, B., Katai, T., and Chance, B. 1994. *Biophys J.* 67, 2501-2510.
Capla, J. M. et al. 2007. *Plastic Reconstructive Surgery* 119, 59-70.
Castello, P. R., David, P. S., McClure, T., Crook, Z., and Poyton, R. O. (2006). *Cell Metabolism* 3, 277-287.
Chandel, N. S., McClintock, D. S., Feliciano, C. E., Wood, T. M., Melendez, J. A., Rodriguez, A. M., and Schumacker, P. T. (2000).
Conlan, M. J., Rapley, J. W., and Cobb, C. M. 1996. *J. Clin. Periodont.* 23, 492-496.
DCCT. 1993. The Diabetes Control and Complications Trial Research Group. *New Eng. J. Med.* 329, 977-986.
DCCT. 1995. *Ann. Neurol.* 38, 869-880.
DCCT/EDIC. 2002. *JAMA* 287, 2563-2569.
Delellis, S., Carnegie, D. E., and Burke, T. J. 2005. *J. Amer. Podiatric Med. Assoc.* 95, 143-147.
Dirmeier, R., O'Brien, K. M., Engle, M., Dodd, A., Spears, E., and Poyton, R. O. (2002). *J. Biol. Chem.* 277, 34773-34784.
Eells, J. Y., Henry, M. M., Summerfelt, P., Wong-Riley, M. T., Buchmann, E. V., Kane, M., Whelan, N. T., and Whelan, H. T. 2004. *Proc. Natl. Acad. Sci. USA*, 100, 3439-3444.
Harkless, L. B., Dellellis, S., Carnegie, D., and Burke, T. J. 2006. *J. Diabetes Complications.* 20, 81-87.
Karu, T. 1999. *J. Photochem. Photobiol.* 49, 1-17.
Karu, T. I., Pyatibrat, L. V., and Kalendo, G. S. 2004. *Photochem Photobiol Sci* 3, 211-216.
Karu, T. I., Pyatibrat, L. V., Kolyakov, S. F. 2005. *Photochem Photobiol.* 81 (2), 98-106.
Lee, I., Salomon, A. R., Ficarro, S., Mathes, I., Lottspeich, F., Grossman, L. I., and Huttemann, M. (2005). *J. Biol. Chem.* 280, 6094-6100.
Lowell, B. B. and Schulman, G. I. 2005. *Science* 307, 384-387.
Palm, F. 2006. *Clinical Experimental Pharmacology and Physiology.* 33, 997-1001.
Pop-Busui, R., Sima, A., and Stevens, M. 2006. *Diabetes Metabolism Research Review.* 22, 257-273.
Powell, M., Carnegie, D. and Burke, T. 2004. *Advances in Skin and Wound Care.* 17, 295-300.
Powell, M. W., Carnegie, D. H., and Burke, T. J. 2006. *Age Ageing* 35, 454.
Poyton, R. O., C. E. Trueblood, R. M. Wright and L. E. Farrell (1988) *Ann. N.Y. Acad. Sci.* 550:289-307.
Poyton, R. O. (1998) Assembling a time bomb—cytochrome c oxidase and disease. *Nature Genetics* 20:316-317.
Poyton, R. O. and J. E. McEwen (1996) *Annu. Rev. Biochem.* 65:563-607.
Prabu, S. K., Anandatheerthavarada, H. K., Raza, H., Srinivasan, S., Spear, J. F., and Avadhani, N. G. (2006). *J. Biol. Chem.* 281, 2061-2070.
Rolo, A. P. and Palmeira, C. M. 2006. *Toxicol and Applied Pharmacology* 212, 167-178.
Ryan, M. T., and Hoogenraar, N. J. 2007. *Annu Rev. Biochem.* 76, 4.1-4.22
Sommer, A. P., Pinheiro, A. L., Mester, A. R., Franke, R. P., and Whelan, H. T. 2001. *J. Clin. Laser Med. Surg.* 19, 29-33.
Tachtsidis, I., Tisdall, M., Leung, T. S., Cooper, C. E., Delpy, D. T., Smith, M., and Elwell, C. E. 2007. *Physiol. Meas.* 28, 199-211.
Takahashi, H., Shin, Y., Cho, S. J., Zago, W. M., Nakamura, T., Gu, Z., Ma, Y., Furukawa, H., Liddington, R., Zhang, D., Tong, G., Chen, H. S., and Lipton, S. A. (2007). *Neuron* 53, 53-64.
Whelan et al. 2001. *J. Clin. Laser Med. Surg.* 19, 305-314.
Whelan et al. 2002. *J. Clin. Laser Med. Surg.* 20, 319-324.
Winterle, J. S., and Einarsdottir, O. 2006. *Photochem Photobiol.* 82: 711-719.
Wong-Riley, M. T., Bai, X., Buchmann, E., and Whelan, H. T. 2001. *Neuroreport* 12, 3033-3037.
Wong-Riley, M. T. T., Liang, H. L., Eelles, J. T., Chance, B., Henry, M. M., Buchmann, E., Kane, M., and Whelan, H. T. 2005. *J. Biol. Chem.* 280, 4761-4771.
Yu, W., Naim, J. O., and Lanzafame, R. J. 1997. *Lasers Surg. Med.* 20, 56-63.

The references cited herein are hereby incorporated by reference in their entirety. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

What is claimed is:

1. A method of treating hypoxia in a hypoxic tissue of a mammalian subject, said method comprising exposing the hypoxic tissue of the mammal to electromagnetic radiation in the visible portion of the spectrum from about 550 nm to about 625 nm substantially free of radiation in the portion of the spectrum from about 630 nm to 700 nm, thereby increasing NO production by mitochondria of the exposed hypoxic tissue, thereby treating hypoxia in the hypoxic tissue.

2. The method of claim 1 wherein the method includes assessing a response to the treatment by measuring blood flow within the hypoxic tissue.

3. The method of claim 1 wherein the method includes assessing a response to the treatment by monitoring blood or tissue levels of NO or an NO-induced vasodilator or vascular endothelial growth factor.

4. The method of claim 1 wherein blood flow in the exposed tissue increases.

5. The method of claim 1 wherein mitochondrial oxygen efficiency in the exposed tissue is increased by the exposure.

6. The method of claim 1 wherein the hypoxia is due to poor circulation in the extremities.

7. The method of claim 1 wherein the subject has diabetes.

8. The method of claim 1 wherein the radiation in the visible portion of the spectrum from about 550 nm to about 625 nm comprises wavelengths from 575 to 600 nm.

9. The method of claim 1 wherein 1 to 20 joules/cm² of the radiation in the visible portion of the spectrum from about 550 nm to about 625 nm is applied.

10. A method of reducing oxidative stress in a tissue of a mammal, said method comprising exposing the tissue to electromagnetic radiation in the visible portion of the spectrum from about 550 nm to about 625 nm substantially free of radiation in the portion of the spectrum from about 630 nm to 700 nm, thereby increasing NO in the tissue, and thereby reducing oxidative stress in the tissue.

11. The method of claim 10 wherein there is a reduction in any one or more of induced oxidative stress genes, levels of lipid peroxides, oxidized nucleosides and oxidized amino acids or polypeptides in the tissue.

12. The method of claim 10 wherein the radiation in the visible portion of the spectrum from about 550 nm to about 625 nm comprises wavelengths from 575 to 600 nm.

13. The method of claim 10 wherein 1 to 20 joules/cm² of the radiation in the visible portion of the spectrum from about 550 nm to about 625 nm is applied.

14. An in vivo or in vitro method of increasing NO production by neurons or endothelial cells in a mammalian tissue capable of producing NO under hypoxic conditions and high concentrations of glucose by cytochrome c nitrite reductase activity, said method comprising exposing the neurons or endothelial cells capable of producing NO under hypoxic conditions and high concentrations of glucose by cytochrome c nitrite reductase activity to electromagnetic radiation in the visible portion of the spectrum from about 550 nm to about 625 nm substantially free of radiation in the portion of the spectrum from about 630 nm to 700 nm, thereby modulating NO production by the neurons or endothelial cells.

15. The method of claim 14 wherein an extremity is irradiated with the electromagnetic radiation in the visible portion of the spectrum from about 550 nm to about 625 nm substantially free of radiation in the portion of the spectrum from about 630 nm to 700 nm.

16. The method of claim 15 wherein the extremity is the foot or hand.

17. The method of claim 15 wherein the extremity is a lower limb.

18. The method of claim 14 wherein the radiation in the visible portion of the spectrum from about 550 nm to about 625 nm comprises wavelengths from 575 to 600 nm.

19. The method of claim 14 wherein 1 to 20 joules/cm² of the radiation in the visible portion of the spectrum from about 550 nm to about 625 nm is applied.

* * * * *